(12) United States Patent
Sessa

(10) Patent No.: US 7,888,089 B2
(45) Date of Patent: Feb. 15, 2011

(54) ENOS MUTATIONS USEFUL FOR GENE THERAPY AND THERAPEUTIC SCREENING

(75) Inventor: William C. Sessa, Madison, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/316,128

(22) Filed: Dec. 9, 2008

(65) Prior Publication Data

US 2009/0246183 A1    Oct. 1, 2009

Related U.S. Application Data

(60) Continuation of application No. 10/889,121, filed on Jul. 12, 2004, now abandoned, which is a division of application No. 09/956,699, filed on Sep. 20, 2001, now Pat. No. 6,900,038, which is a continuation of application No. PCT/US00/09913, filed on Apr. 14, 2000.

(60) Provisional application No. 60/129,550, filed on Apr. 16, 1999.

(51) Int. Cl.
*C12N 9/02* (2006.01)
*C12N 1/20* (2006.01)
*C12N 15/00* (2006.01)
*C12P 21/04* (2006.01)
*C07H 21/04* (2006.01)

(52) U.S. Cl. ............ 435/189; 435/440; 435/69.1; 435/252.3; 435/320.1; 536/23.2

(58) Field of Classification Search ............ None
See application file for complete search history.

(56) References Cited

PUBLICATIONS

Branden et al. Introduction to Protein Structure, Garland Publishing Inc., New York, p. 247, 1991.*
Charles et al. Cloning, characterization, and expression of a cDNA encoding an inducible nitric oxide synthase from the human chondrocyte. Proc Natl Acad Sci USA. Dec 1, 1993;90(23):11419-23.*

* cited by examiner

*Primary Examiner*—Yong D Pak
(74) *Attorney, Agent, or Firm*—Riverside Law LLP

(57) ABSTRACT

The present invention relates to new NOS variants or mutants which contain structural alterations in the site of Akt dependent phosphorylation. The altered NOS proteins or peptides, especially the human eNOS proteins or peptides, Akt proteins or polypeptides and their encoding nucleic acid molecules are useful as gene therapy agents for the treatment of diseases including post angioplasty restenosis, hypertension, atherosclerosis, heart failure, diabetes and diseases with defective angiogenesis. NOS proteins and peptides are also useful in methods of screening for agents which modulate NOS activity.

5 Claims, 13 Drawing Sheets

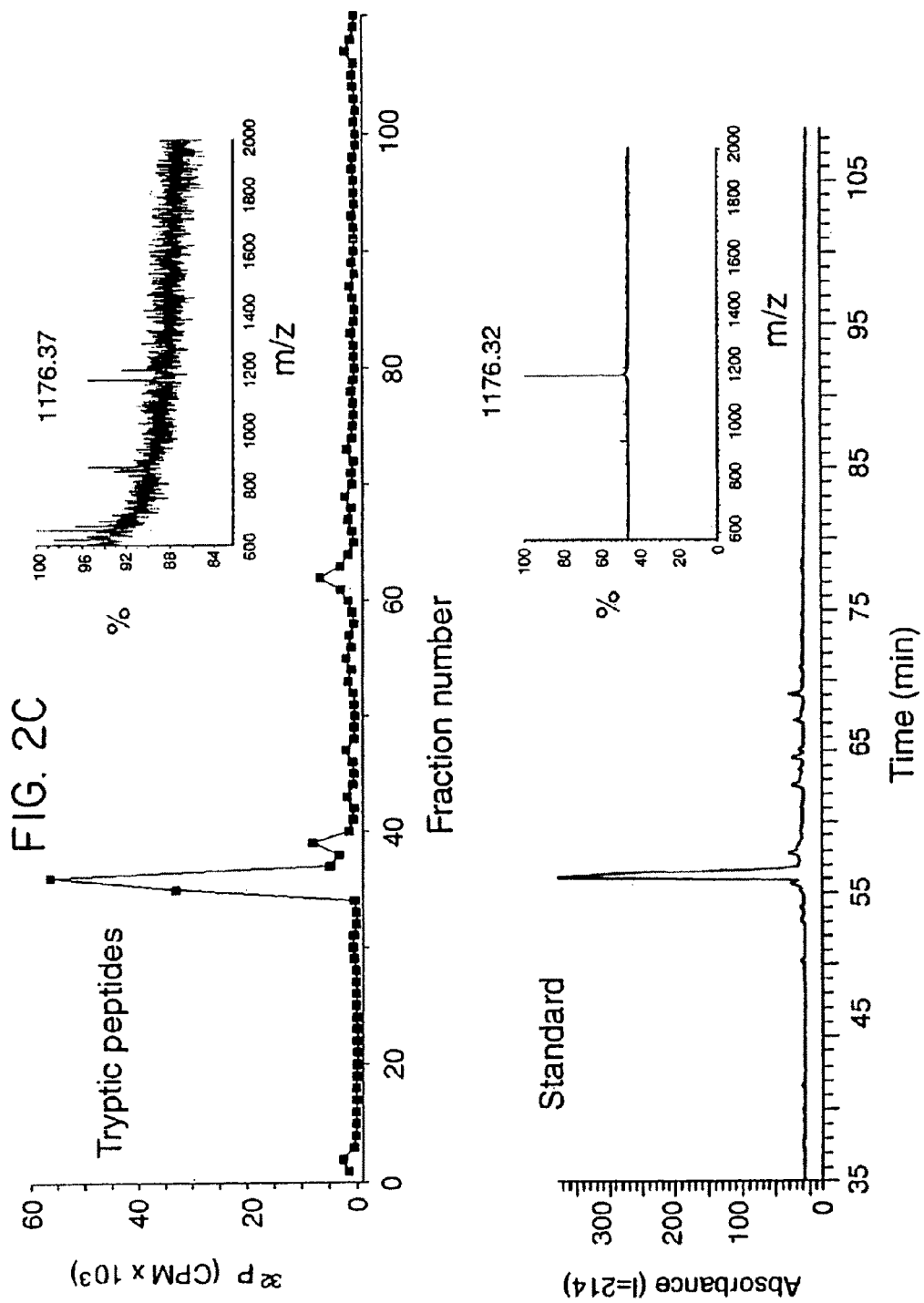

FIG. 5A
FIG. 5B
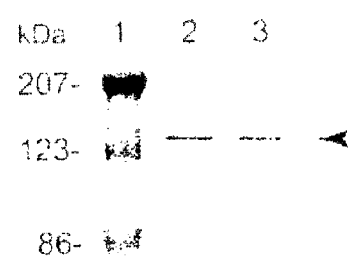
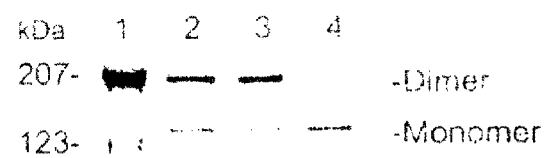

ENOS MUTATIONS USEFUL FOR GENE THERAPY AND THERAPEUTIC SCREENING

CROSS REFERENCES TO RELATED APPLICATIONS

This application is a continuation of U.S. application Ser. No. 10/889,121, filed Jul. 12, 2004 which is a divisional of U.S. application Ser. No. 09/956,699, filed on Sep. 20, 2001, now issued U.S. Pat. No. 6,900,038, which is a continuation of PCT/US00/09913, filed Apr. 14, 2000, which claims the benefit under 35 U.S.C. §119(e) of U.S. Provisional Application No. 60/129,550, filed Apr. 16, 1999, all of which are herein incorporated by reference in their entirety.

ACKNOWLEDGMENT OF FEDERAL SUPPORT

The present invention arose in part from research funded by the following federal grant monies: HL 57665 and HL 61371.

TECHNICAL FIELD

The present invention relates to new NOS variants or mutants which contain structural alterations in the site of Akt dependent phosphorylation. The altered NOS proteins or peptides and their encoding nucleic acid molecules are useful as gene therapy agents for the treatment of diseases including post angioplasty restenosis, hypertension, atherosclerosis, heart failure, diabetes and diseases with defective angiogenesis.

BACKGROUND OF THE INVENTION

Atherosclerosis and vascular thrombosis are a major cause of morbidity and mortality, leading to coronary artery disease, myocardial infarction, and stroke. Atherosclerosis begins with an alteration in the endothelium which lines the blood vessels. An endothelial alteration may eventually result in the development of an endothelial lesion caused, in part, by the uptake of oxidized low-density lipoprotein (LDL) cholesterol. Rupture of this lesion can lead to thrombosis and occlusion of the blood vessel. In the case of a coronary artery, rupture of a complex lesion may precipitate a myocardial infarction, whereas in the case of a carotid artery, stroke may ensue.

In atherosclerotic coronary heart disease, endothelial dysfunction may diminish production of vasodilatory substances, such as nitric oxide. Myocardial ischemia results when autoregulatory vasodilation is prevented, whether by flow-limiting coronary arterial stenosis or by endothelial dysfunction. In both cases, arterial blood flow can no longer increase proportional to rising oxygen demands. In other situations, myocardial ischemia may occur when oxygen demands are constant but there is a primary decrease in coronary blood flow mediated via coronary artery spasm, rapid evolution of the underlying atherosclerotic plaque leading to a reduced coronary arterial lumen caliber, and/or intermittent microvascular plugging by platelet aggregates.

Balloon angioplasty is commonly used to reopen a blood vessel which is narrowed by plaque. Although balloon angioplasty is successful in a high percentage of the cases in opening the vessel, it often denudes the endothelium and injures the vessel in the process. This damage causes the migration and proliferation of vascular smooth muscle cells of the blood vessel into the area of injury to form a lesion, known as myointimal hyperplasia or restenosis. This new lesion leads to a recurrence of symptoms within three to six months after the angioplasty in a significant proportion of patients.

In atherosclerosis, thrombosis and restenosis there is also a loss of normal vascular function, such that vessels tend to constrict, rather than dilate. The excessive vasoconstriction of the vessel causes further narrowing of the vessel lumen, limiting blood flow. This can cause symptoms such as angina (if a heart artery is involved), or transient cerebral ischemia (i.e. a "small stroke", if a brain vessel is involved). This abnormal vascular function (excessive vasoconstriction or inadequate vasodilation) occurs in other disease states as well. Hypertension (high blood pressure) is caused by excessive vasoconstriction, as well as thickening, of the vessel wall, particularly in the smaller vessels of the circulation. This process may affect the lung vessels as well causing pulmonary (lung) hypertension. Other disorders known to be associated with excessive vasoconstriction, or inadequate vasodilation include transplant atherosclerosis, congestive heart failure, toxemia of pregnancy, Raynaud's phenomenon, Prinzmetal's angina (coronary vasospasm), cerebral vasospasm, hemolytic-uremia and impotence.

A substance released by the endothelium, initially referred to as "endothelium derived relaxing factor" (EDRF), plays an important role in inhibiting these pathologic processes. EDRF is now known to be nitric oxide (NO). NO plays many roles in human physiology, including the relaxation of vascular smooth muscle, the inhibition of platelet aggregation, the inhibition of mitogenesis, the proliferation of vascular smooth muscle, and leukocyte adherence. Because NO is the most potent endogenous vasodilator, and because it is largely responsible for exercise-induced vasodilation in the conduit arteries, enhancement of NO synthesis could also improve exercise capacity in normal individuals and those with vascular disease.

Endothelial nitric oxide synthase (eNOS) is the nitric oxide synthase (NOS) isoform responsible for the maintenance of systemic blood pressure, vascular remodeling and angiogenesis (Shesely et al., 1996; Huang et al., 1995; Rudic et al., 1998; Murohara et al., 1998). As deficient endothelial production of NO is an early, persistent feature of atherosclerosis and vascular injury, eNOS has proven to be an attractive target for vascular gene therapy. While the regulation of eNOS activation remains largely undefined, it is known that eNOS is phosphorylated in response to various forms of cellular stimulation (Michel et al., 1993; Garcia-Cardena et al., 1996; Corson et al., 1996), however, the role of phosphorylation in the regulation of nitric oxide (NO) production and the kinase(s) responsible has not been previously elucidated.

SUMMARY OF THE INVENTION

The present inventions result, in part, from the new discovery that the serine/threonine protein kinase, Akt (protein kinase B), can directly phosphorylate eNOS on a serine residue corresponding to residue 1179 in bovine eNOS or residue 1177 in human eNOS and activate the enzyme leading to NO production. Mutant eNOS (S1179A or S1177A) is resistant to Akt phosphorylation and activation while mutant eNOS (S1179D and S1177D) or (S1179E and S1177E) is constitutively active. Moreover, using adenoviral mediated gene transfer activated Akt increases basal NO release from endothelial cells and activation deficient Akt attenuates VEGF stimulated NO production. Thus, eNOS is a newly described Akt substrate linking signal transduction via Akt to the release of the gaseous second messenger, NO. The present inventions are also based in part on the findings that mutant eNOS (S1179D) exhibits an increase in the rate of NO production and an increase in reductase activity.

The present invention includes NOS, polypeptides or proteins and their encoding isolated nucleic acid molecules, wherein the NOS polypeptide or protein contains a substituted amino acid residue corresponding to residue 1179 of bovine eNOS, residue 1177 of human eNOS, residue 1412 of rat nNOS, or residue 1415 at human nNOS. Preferred substitutions include amino acids with negatively charged R groups, including aspartic acid and glutamic acid.

The present invention also includes NOS polypeptides or proteins and their encoding isolated nucleic acid molecules, wherein the NOS polypeptide or protein contains a substituted amino acid residue corresponding to residue 1179 of bovine eNOS, residue 1177 of human eNOS, residue 1412 of rat nNOS, or residue 1415 at human nNOS. Preferred substitutions include amino acids with non-negatively charged R groups, such as alanine.

The present invention provides methods for stimulating collateral vessel development in ischemic diseases with deficient endogenous angiogenesis, specifically peripheral vascular disease and/or myocardial ischemia in a patient comprising delivering a transgene coding for an NOS polypeptide of the invention or an Akt polypeptide.

The invention further includes a non-human transgenic animal which express an NOS polypeptide of the invention.

Lastly, the invention includes methods of identifying an agent which modulates the Akt regulated activity of NOS, comprising the general steps of: (a) exposing purified NOS, preferably eNOS or nNOS, or a cell that expresses NOS, preferably eNOS or nNOS, and Akt to an agent; and (b) measuring the Akt regulated activity of NOS, preferably eNOS or nNOS.

BRIEF DESCRIPTION OF THE DRAWINGS

In FIG. 1A, COS cells were transfected with plasmids for eNOS, in the absence or presence of Akt or kinase inactive Akt (K179M) and the production of NO (assayed as $NO_2^-$) determined by chemiluminescence. In FIG. 1B, COS cells were transfected with various NOS plasmids as above. In both FIG. 1A and FIG. 1B, values for $NO_2^-$ production were subtracted from levels obtained from cells transfected with the β-galactosidase cDNA only. The inset shows the expression of proteins in total cell lysates. Data are mean±SEM, n=3-7 experiments; * denotes p<0.05.

FIGS. 2A-2D. Phosphorylation of eNOS by active Akt in vitro and in vivo. In FIG. 2A, COS cells were transfected with HA-Akt or HA-Akt(K179M), lysates were immunoprecipitated and placed into an in vitro kinase reaction with histone 2B (25 mg) or recombinant eNOS (3 mg) as substrates. The top panel depicts the incorporation of $^{32}P$ into the substrates and the bottom panel shows the amount of substrate by Coomassie staining of the gel. In FIG. 2B, $^{32}P$ labeled wild-type or the double serine mutant of eNOS (eNOS S635/1179) was affinity purified from transfected COS cells and subjected to autoradiography (upper panel) or Western blotting (lower panel). The graphical data in FIG. 2B reflects the relative amount of labeled protein to the amount of immunoreactive eNOS in the gel. In FIG. 2C, labeled eNOS was digested with trypsin and peptides separated by RP-HPLC. The upper chromatogram documents a predominant labeled tryptic peptide that co-migrates with a unlabeled synthetic phosphopeptide standard (bottom chromatogram). The insets demonstrate by linear mode MS of labeled peptide (top) and phosphopeptide standard identical mass ions. In FIG. 2D, recombinant wild-type eNOS or eNOS S1179A were purified and equal amounts (2.4 mg) placed into an in vitro kinase reaction with recombinant Akt as described in Methods. The top panel in FIG. 2D depicts the incorporation of $^{32}P$ into eNOS and the bottom panel shows the amount of substrate by Coomassie staining of the gel. The graphical data (n=3) reflects the relative amount of labeled eNOS to the mass of eNOS (Coomassie) in the in vitro kinase reaction.

In FIG. 4A, BLMVEC were infected with adenoviral constructs (β-gal as control, myrAkt and AA-Akt) and the amount of $NO_2^-$ produced over 24 hrs determined (n=3). The inset shows the expression of eNOS and Akt. In FIG. 4B, lysates from adenoviral infected BLMVEC were examined for NOS activity. Equal amounts of protein (50 mg) were incubated with various concentrations of free calcium and NOS activity determined (n=3 experiments). In FIG. 4C, BLMVEC were infected with adenoviruses as above followed by stimulation with VEGF (40 ng/ml) for 30 min and $NO_2^-$ release quantified by chemiluminescence. Data are presented as VEGF stimulated release of $NO_2^-$ after subtraction of basal levels. Data are mean±SEM, n=4; * represent significant differences (p<0.05).

FIGS. 5A and 5B. Purity and dimer/monomer ratio of wild type and eNOS S1179D. In A and B, SDS-PAGE analysis was performed on 7.5% polyacrylamide gels stained with Coomassie Blue. Molecular mass standards (lane 1) and their size in kDa are indicated at the left. Wild type eNOS (lane 2) and eNOS S1179D (lane 3) (1 μg of each) were resolved as indicated by arrowheads. In B, proteins (2 μg of each) were resolved on SDS-PAGE run at 4° C. Molecular mass standards were in lane 1. Nonboiled samples of wild type and eNOS S1179D were resolved in lanes 2 and 3, respectively. In lane 4, wild type-eNOS was boiled in SDS sample buffer.

DETAILED DESCRIPTION OF THE INVENTION

A. General Description

Figure 1A:
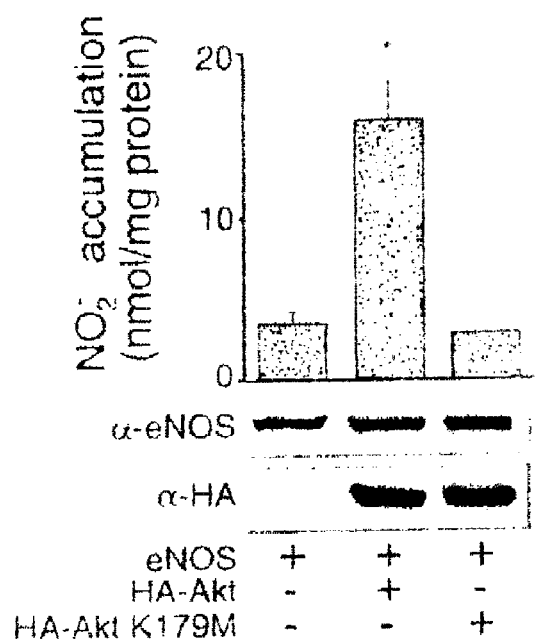
FIGS. 1A-1B. Wild-type Akt, but not kinase inactive Akt increases NO release from cells expressing membrane associated eNOS.

The present inventions are based, in part, upon the discovery that the serine/threonine protein kinase, Akt (protein kinase B), can directly phosphorylate eNOS on serine 1179 (serine 1177 in human eNOS), and activate the enzyme leading to NO production while mutant eNOS (S1179A) is resistant to Akt phosphorylation and activation. Moreover, using adenoviral mediated gene transfer activated Akt increases basal NO release from endothelial cells and activation deficient Akt attenuates VEGF stimulated NO production. Thus, eNOS is a newly described Akt substrate linking signal transduction via Akt to the release of the gaseous second messenger, NO. The present inventions are also based in part on the findings that mutant eNOS, for instance, S1179D, exhibits an increase in the rate of NO production and an increase in reductase activity.

The demonstration that NO production is regulated by Akt dependent phosphorylation of eNOS provides novel constitutively active eNOS mutants for use in gene therapy aimed at improving endothelial function in cardiovascular diseases associated with dysfunction in the synthesis or biological activity of NO. Such diseases include post angioplasty restenosis, hypertension, atherosclerosis, heart failure including myocardial infarction, diabetes, and diseases with defective angiogenesis. This discovery also provides a novel therapeutic target useful for the design of drugs useful for treating diseases associated with dysfunction in the synthesis or biological activity of NO.

The present invention also provides novel constitutively active nNOS mutants which have a substituted amino acid corresponding to residue 1412 of rat nNOS or 1415 or human nNOS for use in gene therapy aimed at the treatment of diseases.

B. Specific Embodiments

Production of NOS Mutant Proteins or Polypeptides

The present invention provides NOS proteins or polypeptides, allelic variants of NOS proteins, and conservative amino acid substitutions of NOS proteins, all of which contain a mutation of a serine residue which is the site of Akt mediated phosphorylation. For instance, the proteins or polypeptides of the invention include but are not limited to: (1) human eNOS proteins which comprise a mutation of residue 1177 (Janssens et al. (1992) *J. Biol. Chem.* 267: 14519-14522 which is herein incorporated by reference in its entirety) from a serine to another amino acid, such as alanine, and are resistant to Akt mediated phosphorylation; (2) bovine eNOS proteins which comprise a mutation of residue 1179 (SEQ ID NO: 2 of U.S. Pat. No. 5,498,539, which is herein incorporated by reference in its entirety) from a serine to another amino acid, such as alanine, and are resistant to Akt mediated phosphorylation; (3) human nNOS proteins which comprise a mutation of residue 1415 from a serine to another amino acid, such as alanine, and are resistant to Akt mediated phosphorylation; (4) rat nNOS proteins which comprise a mutation of residue 1412 from a serine to another amino acid, such as alanine, and are resistant to Akt mediated phosphorylation; (5) human eNOS proteins which comprise a mutation of residue 1177 from a serine to an amino acid containing a negatively charged R group, such as aspartic or glutamic acid, and are constitutively active and exhibit increased NO production and increased reductase activity; (6) bovine eNOS proteins which comprise a mutation of residue 1179 from a serine to an amino acid containing a negatively charged R group, such as aspartic or glutamic acid, and are constitutively active and exhibit increased NO production and increased reductase activity; (7) human nNOS proteins which comprise a mutation of residue 1415 from a serine to an amino acid containing a negatively charged R group, such as aspartic or glutamic acid, and are constitutively active and exhibit increased NO production and increased reductase activity; (8) rat nNOS proteins which comprise a mutation of residue 1412 from a serine to an amino acid containing a negatively charged R group, such as aspartic or glutamic acid, and are constitutively active and exhibit increased NO production and increased reductase activity; and (9) NOS proteins from species other than humans, cows, or rat which are modified to contain an amino acid other than serine at a position corresponding to the serine at position 1177 in the human eNOS or position 1179 in the bovine eNOS, position 1412 in the rat nNOS, and position 1415 in the human nNOS and which are either resistant to Akt phosphorylation, are constitutively active, or exhibit increased NO production and increased reductase activity. NOS mutants may also be produced by mutating other amino acids in the phosphorylation motif RXRXXS/T.

The present invention provides constitutively active NOS polypeptides, preferably eNOS or nNOS, exhibiting increased NO production and reductase activity and comprising a mutation at the serine residue at the site of Akt mediated phosphorylation. It is also within the skill of the artisan to obtain conservative variants such as substitutions, deletions, and insertions mutants of these NOS polypeptides exhibiting increased NO production and reductase activity. As used herein, a conservative variant refers to alterations in the amino acid sequence that do not adversely affect the ability of constitutively active NOS, preferably eNOS or nNOS, to produce NO or the reductase activity of constitutively active NOS, preferably eNOS or nNOS. A substitution, insertion, or deletion is said to adversely affect constitutively active NOS polypeptide, when the altered sequence affects the ability of constitutive NOS, such that it does not produce NO at an increased level and does not have increased reductase activity as compared to the wild-type NOS. For example, the overall charge, structure or hydrophobic/hydrophilic properties of constitutive NOS can be altered without adversely affecting the activity of constitutive NOS. Accordingly, the amino acid sequence of NOS polypeptide can be altered, for instance to render the polypeptide more hydrophobic or hydrophilic, without adversely affecting the activity of NOS.

As used herein, a "constitutively active" mutant or variant of NOS, whether modified or isolated from a natural source, refers to a NOS protein, preferably an eNOS or a nNOS, which produces NO at a rate higher than native NOS containing a serine in its unphosphorylated form at an amino acid residue corresponding to residue 1177 in human NOS or residue 1179 in bovine NOS. Preferred constitutively active variants comprise an amino acid with a negatively charged R group, such as aspartic or glutamic acid, at the amino acid residue corresponding to the serine at position 1177 in the human eNOS or position 1179 in the bovine NOS.

The present invention provides NOS proteins or polypeptides, allelic variants of NOS proteins, and conservative amino acid substitutions of NOS proteins that contain a substituted amino acid residue corresponding to residue 1177 of bovine eNOS, to residue 1179 of human eNOS, to residue 1412 of rat nNOS, and to residue 1415 of human nNOS, wherein the substituted amino acid residue comprises a non-negatively charged R group, such as alanine.

The NOS proteins, preferably eNOS or nNOS proteins, of the present invention may be in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

Also included in the invention are NOS peptides which span the Akt phosphorylation site corresponding to residue 1179 in bovine eNOS, residue 1177 in human eNOS, residue 1412 in rat nNOS or residue 1415 in human nNOS. Peptides may contain a serine at the phosphorylation site or, preferably, may contain a substitution of the serine at position corresponding to residue 1179 in bovine eNOS, residue 1177 in human eNOS, residue 1412 in rat nNOS, or residue 1415 in human nNOS. Such substitutions include, but are not limited to, amino acids with an R group that mimics serine in its phosphorylated state, such as aspartic acid or glutamic acid. Such substitutions also include, amino acids with a non-negative R group, such as alanine. Peptides spanning this site may be about 3, 5, 7, 10, 12, 15, 17, 20, 25, 30, 40, 50 or more amino acids in length.

NOS proteins, polypeptides or peptides of the invention may be prepared by any means available, including recombinant expression from an NOS cDNA which has been modified to replace or alter the nucleotide triplet encoding a serine corresponding to the serine at position 1177 in the human eNOS, position 1179 in the bovine eNOS, residue 1412 in rat nNOS, or residue 1415 in human nNOS. Any available technique may be used to mutate the nucleotide triplet encoding the serine residue, such as homologous recombination, site-directed mutagenesis or PCR mutagenesis (see, Sambrook et al., Molecular Cloning, Cold Spring Harbor Laboratory Press, 1989). Starting cDNAs may include the human and bovine eNOS cDNAs as well as cDNAs encoding eNOS proteins of other animal species, including but not limited to rabbit, rat, murine, porcine, ovine, equine and non-human primate species.

As used herein, a nucleic acid molecule encoding a NOS protein or polypeptide, preferably eNOS or nNOS protein or polypeptide, of the invention is said to be "isolated" when the nucleic acid molecule is substantially separated from contaminant nucleic acid encoding other polypeptides from the source of nucleic acid.

The present invention further provides fragments of the encoding nucleic acid molecule. As used herein, a fragment of an encoding nucleic acid molecule refers to a small portion of the entire protein encoding sequence. The size of the fragment will be determined by the intended use. For example, if the fragment is chosen so as to encode an active portion of the protein, the fragment will need to be large enough to encode the functional region(s) of the protein, including the Akt phosphorylation site. If the fragment is to be used as a nucleic acid probe or PCR primer, then the fragment length is chosen so as to obtain a relatively small number of false positives during probing/priming to a region which spans or flanks the NOS Akt phosphorylation site.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci, et al. 1981 *J. Am. Chem. Soc.* 103:3185-3191) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

The present invention further provides recombinant DNA molecules (rDNAs) that contain an NOS coding sequence as described above. As used herein, a rDNA molecule is a DNA molecule that has been subjected to molecular manipulation. Methods for generating rDNA molecules are well known in the art, for example, see Sambrook et al., *Molecular Cloning* (1989). In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pPL and pKK223 available from Pharmacia, Piscataway, N.J.

Expression vectors compatible with eukaryotic cells, preferably those compatible with vertebrate cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al. (1982) *J. Mol. Anal. Genet.* 1:327-341) Alternatively, the selectable marker can be present on a separate plasmid, and the two vectors are introduced by co-transfection of the host cell, and selected by culturing in the appropriate drug for the selectable marker.

The present invention further provides host cells transformed or transfected with a nucleic acid molecule that encodes an NOS protein, preferably eNOS or nNOS protein, of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines. Any prokaryotic host can be used to express a rDNA molecule encoding a protein of the invention. The preferred prokaryotic host is *E. coli*, particularly for the constitutively active NOS mutants.

Transformation or transfection of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., (1972) *Proc. Natl. Acad. Sci. USA* 69:2110; and Maniatis et al., *Molecular Cloning, A Laboratory Mammal*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al. 1983) *Virol.* 52:456; Wigler et al., (1979) *Proc. Natl. Acad. Sci. USA* 76:1373-76. Successfully transformed or transfected cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern (1975) *J. Mol. Biol.* 98:503 or Berent et al. (1985) *Biotech.* 3:208, or the proteins produced from the cell assayed via an immunological method.

The present invention further provides methods for producing a NOS protein, preferably an eNOS protein or a nNOS protein, of the invention using nucleic acid molecules herein described. In general terms, the production of a recombinant form of a protein typically involves the following steps. A nucleic acid molecule is first obtained that encodes a protein of the invention. If the encoding sequence is uninterrupted by introns, it is directly suitable for expression in any host. The nucleic acid molecule is then preferably placed in operable linkage with suitable control sequences, as described above, to form an expression unit containing the protein open reading frame. The expression unit is used to transform or transfect a suitable host and the transformed or transfected host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation or transfection methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

Gene Therapy

Any appropriate gene delivery system combined with a suitable gene expression system using the most appropriate route of delivery is encompassed by the present invention. For instance, NOS mutant or variant genes, preferably eNOS or nNOS mutant or variant genes, of the invention or Akt genes may be transferred to the heart (or skeletal muscle), including cardiac myocytes (and skeletal myocytes), in vitro or in vivo to direct production of the encoded protein. Particularly useful are human Akt genes and NOS mutants, preferably human eNOS, containing an amino acid with a negatively charged R group, such as aspartic or glutamic acid, at a position corresponding to serine 1177 in human eNOS. Routes of administering NOS mutant or variant genes include, but are not limited to, intravascular, intramuscular, intraperitoneal, intradermal, and intraarterial injection.

The adenovirus gene delivery system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection. A preferred delivery vector is a helper-independent replication deficient human adenovirus 5, although other delivery means are available and may be used, including delivery of nucleic acids directly to the cells of interest (see Sawa et al. (1998) *Gene Ther.* 5(11):1472-80; Labhasetwar et al. (1998) *J. Pharm. Sci.*87(11):1347-50; Lin et al (1997) *Hypertension* 30:307-313; Chen et al. (1997) *Circ. Res.* 80(3):327-335; Channon et al (1996) *Cardiovasc. Res.* 32:962-972; *Harv Heart Lett.* (1999) 9(8):5-6; and Nabel et al. (1999) *Nat. Med.* 5(2):141-2.

Using the adenovirus 5 system, transfection frequencies of greater than 60% have been demonstrated in myocardial cells in vivo by a single intracoronary injection (Giordano and Hammond (1994) *Clin. Res.* 42: 123A). Non-replicative recombinant adenoviral vectors are particularly useful in transfecting coronary endothelium and cardiac myocytes resulting in highly efficient transfection after intracoronary injection. Non-replicative recombinant adenoviral vectors are also useful for transfecting desired cells of the peripheral vascular system (see U.S. Pat. No. 5,792,453, which is herein incorporated by reference in its entirety).

Adenoviral vectors used in the present invention can be constructed by the rescue recombination technique described in Graham et al. (1988) *Virology* 163:614-617. Briefly, the eNOS transgene is cloned into a shuttle vector that contains a promoter, polylinker and partial flanking adenoviral sequences from which E1A/E1B genes have been deleted. As the shuttle vector, plasmid pAC1 (*Virology* 163:614-617, 1988) (or an analog) which encodes portions of the left end of the human adenovirus 5 genome (Virology 163:614-617, 1988) minus the early protein encoding E1A and E1B sequences that are essential for viral replication, and plasmid ACCMVPLPA (*J. Biol. Chem.* 267:25129-25134, 1992) which contains polylinker, the CMV promoter and SV40 polyadenylation signal flanked by partial adenoviral sequences from which the EA/E1B genes have been deleted can be exemplified. The use of plasmid PAC1 or ACCMV-PLA facilitates the cloning process. The shuttle vector is then co-transfected with a plasmid which contains the entire human adenoviral 5 genome with a length too large to be encapsidated, into 293 cells. Co-transfection can be conducted by calcium phosphate precipitation or lipofection (*Biotechniques* 15:868-872, 1993). Plasmid JM17 encodes the entire human adenovirus 5 genome plus portions of the vector pBR322 including the gene for ampicillin resistance (4.3 kb). Although JM17 encodes all of the adenoviral proteins necessary to make mature viral particles, it is too large to be encapsidated (40 kb versus 36 kb for wild type). In a small subset of co-transfected cells, rescue recombination between the transgene containing the shuttle vector such as plasmid pAC1 and the plasmid having the entire adenoviral 5 genome such as plasmid pJM17 provides a recombinant genome that is deficient in the E1A/E1B sequences, and that contains the transgene of interest but secondarily loses the additional sequence such as the pBR322 sequences during recombination, thereby being small enough to be encapsidated. The CMV driven beta-galactosidase encoding adenovirus HCMVSP1lacZ (*Clin. Res.* 42: 123A, 1994) can be used to evaluate efficiency of gene transfer using X-gal treatment.

In another embodiment, the gene encoding NOS, preferably eNOS or nNOS, may be introduced in vivo via an attenuated or defective DNA virus, such as but not limited to herpes simplex virus (HSV), papillomavirus, Epstein Barr virus (EBV), adenovirus, and adeno-associated virus (AAV). Defective viruses, which entirely or almost entirely lack viral genes, are preferred. Defective virus is not infective after introduction into a cell. Use of defective, vital vectors allows for administration to cells in a specific, localized area, without concern that the vector can infect other cells. Thus, a particular locus, e.g., in the brain or spinal chord, can be specifically targeted with the vector. In a specific embodiment, a defective herpes virus 1 (HSV1) vector may be used (Kaplitt et al. (1991) *Molec. Cell. Neurosci.* 2:320-330). In yet another embodiment, the viral vector is an attenuated adenovirus vector, such as the vector described by Stratford-Perricaudet et al. (*J. Clin. Invest.* 90:626-630 (1992)). In a yet a further embodiment, the vector is a defective adeno-associated virus vector (Samulski et al. (1987) *J. Virol.* 61:3096-3101; Samulski et al. (1989) *J. Virol.* 63:3822-3828).

The present invention also contemplates the use of cell targeting not only by delivery of the transgene into the coronary artery, or femoral artery, for example, but also the use of tissue-specific promoters. By fusing, for example, tissue-specific transcriptional control sequences of left ventricular myosin light chain-2 (MLC[2V]) or myosin heavy chain (MHC) to a transgene such as the NOS genes of the invention within the adenoviral construct, transgene expression is limited to ventricular cardiac myocytes. The efficacy of gene expression and degree of specificity provided by MLC[2V] and MHC promoters with lacZ have been determined, using the recombinant adenoviral system of the present invention. Cardiac-specific expression has been reported previously by Lee et al. (*J. Biol. Chem.* 267:15875-15885 (1992)). The MLC[2V] promoter is comprised of 250 bp, and fits easily within the adenoviral-5 packaging constraints. The myosin heavy chain promoter, known to be a vigorous promoter of transcription, provides a reasonable alternative cardiac-specific promoter and is comprised of less than 300 bp. Smooth muscle cell promoters such as SM22 alpha promoter (Kemp et al., (1995) *Biochem J* 310 (Pt 3):103743) and SM alpha actin promoter (Shimizu et al (1995) *J Biol Chem* 270(13): 7631-43) are also available. Other promoters, such as the troponin-C promoter, while highly efficacious and sufficiently small, lacks adequate tissue specificity. By using the MLC[2V] or MHC promoters and delivering the transgene in vivo, it is believed that the cardiac myocyte alone (that is without concomitant expression in endothelial cells, smooth muscle cells, and fibroblasts within the heart) will provide adequate expression of the NOS protein.

Limiting expression to the cardiac myocyte also has advantages regarding the utility of gene transfer for the treatment of clinical myocardial ischemia. By limiting expression to the heart, one avoids the potentially harmful effect of angiogenesis in non-cardiac tissues such as the retina. In addition, of the cells in the heart, the myocyte would likely provide the longest transgene expression since the cells do not undergo rapid turnover; expression would not therefore be decreased by cell division and death as would occur with endothelial cells. Endothelial-specific promoters are already available for this purpose. Examples of endothelial specific promoters include the Tie-2 promoter (Schlaeger et al. (1997) *Proc Natl Acad Sci* 1; 94(7):3058-63), the endothelin promoter (Lee et al. (1990) *J. Biol. Chem.* 265:10446-10450), and the eNOS promoter (Zhang et al. (1995) *J. Biol. Chem.* 270(25): 15320-6).

The present invention includes, with regard to the treatment of heart disease, targeting the heart by intracoronary or intramuscular injection with a high titer of the vector and transfecting all cell types is presently preferred. Diseases such as erectile dysfunction and cardiovascular diseases including, mycardial infarction, myocardial ischemia, heart failure, restenosis, stent stenosis, post-angioplasty stenosis, and by-pass graft failure may be treated as described using the NOS transgenes, preferably eNOS or nNOS transgenes.

Successful recombinant vectors can be plaque purified according to standard methods. The resulting viral vectors are propagated on 293 cells which provide E1A and E1B functions in trans to titers in the preferred about $10^{10}$-about $10^{12}$ viral particles/ml range. Cells can be infected at 80% confluence and harvested 48 hours later. After 3 freeze-thaw cycles the cellular debris is pelleted by centrifugation and the virus purified by CsCl gradient ultracentrifugation (double CsCl gradient ultracentrifugation is preferred). Prior to in vivo injection, the viral stocks are desalted by gel filtration through Sepharose columns such as G25 Sephadex. The product is then filtered through a 30 micron filter, thereby reducing deleterious effects of intracoronary injection of unfiltered virus (life threatening cardiac arrhythmias) and promoting efficient gene transfer. The resulting viral stock has a final viral titer in the range of $10^{10}$-$10^{12}$ viral particles/ml. The recombinant adenovirus must be highly purified, with no wild-type (potentially replicative) virus. Impure constructs can cause an intense immune response in the host animal. From this point of view, propagation and purification may be conducted to exclude contaminants and wild-type virus by, for example, identifying successful recombinants with PCR using appropriate primers, conducting two rounds of plaque purification, and double CsCl gradient ultracentrifugation. Additionally, the problems associated with cardiac arrhythmias induced by adenovirus vector injection into patients can be avoided by filtration of the recombinant adenovirus through an appropriately-sized filter prior to intracoronary injection. This strategy also appears to substantially improve gene transfer and expression.

The viral stock can be in the form of an injectable preparation containing pharmaceutically acceptable carrier such as saline, for example, as necessary. The final titer of the vector in the injectable preparation is preferably in the range of about $10^7$-about $10^{13}$ viral particles which allows for effective gene transfer. Other pharmaceutical carriers, formulations and dosages are described below. The adenovirus transgene constructs are delivered to the myocardium by direct intracoronary (or graft vessel) injection using standard percutaneous catheter based methods under fluoroscopic guidance, at an amount sufficient for the transgene to be expressed to a degree which allows for highly effective therapy. The injection may be made deeply into the lumen (about 1 cm within the arterial lumen) of the coronary arteries (or graft vessel), and preferably be made in both coronary arteries, as the growth of collateral blood vessels is highly variable within individual patients. By injecting the material directly into the lumen of the coronary artery by coronary catheters, it is possible to target the gene rather effectively, and to minimize loss of the recombinant vectors to the proximal aorta during injection. It is known that gene expression when delivered in this manner does not occur in hepatocytes and viral RNA cannot be found in the urine at any time after intracoronary injection. Any variety of coronary catheter, or a Stack perfusion catheter, for example, can be used in the present invention. In addition, other techniques known to those having ordinary skill in the art can be used for transfer of NOS genes, preferably eNOS or nNOS, to the arterial wall.

For the treatment of peripheral vascular disease, a disease characterized by insufficient blood supply to the legs, recombinant adenovirus expressing a NOS, preferably an eNOS or a nNOS, peptide or protein of the invention may be delivered by a catheter inserted into the proximal portion of the femoral artery or arteries, thereby effecting gene transfer into the cells of the skeletal muscles receiving blood flow from the femoral arteries.

In instances wherein a transgene or nucleic acid encoding an NOS, preferably an eNOS or a nNOS, or Akt protein of the invention is first transferred to endothelial or vascular smooth muscle cells in vitro, including the patients own cells, DNA may be transfected into the cells directly (see U.S. Pat. No. 5,658,565). Generally, to transfect target cells, a plasmid vector comprising a DNA sequence encoding an Akt or NOS of the invention or a biologically active fragment thereof may be utilized in liposome-mediated transfection of the target cell. The stability of liposomes, coupled with the impermeable nature of these vesicles, makes them useful vehicles for the delivery of therapeutic DNA sequences (for a review, see Mannino and Gould-Forgerite (1988) *BioTechniques* 6(7): 682-690). Liposomes are known to be absorbed by many cell types by fusion. In one embodiment, a cationic liposome containing cationic cholesterol derivatives, such as SF-chol or DC-chol, may be utilized. The DC-chol molecule includes a tertiary amino group, a medium length spacer arm and a carbamoyl linker bond as described by Gao and Huang (*Biochem. Biophys. Res. Comm.* 179: 280-285, 1991).

In another embodiment regarding the use of liposome technology, the viral or nonviral based vector comprising the DNA sequence encoding a biologically active NOS protein fragment, preferably eNOS or nNOS protein fragment, is delivered to the target cell by transfection of the target cell with lipofectamine (Bethesda Research Laboratory). Lipofectamine is a 3:1 Liposome formulation of the polycationic lipid 2,3 dioleyloxy-N-[2(sperminecarboxymido)ethyl]-N, N-dimethyl-1-propanaminiumtric fluoroacetate (DOPSA) and the neutral lipid dioleoly-phosphatidylethanolamine (DOPE).

Other non-viral modes of gene delivery include, but are not limited to: (a) direct injection of naked DNA; (b) calcium phosphate $[Ca_3(PO_4)_2]$ mediated cell transfection; (c) mammalian host cell transfection by electroporation; (d) DEAE-dextran mediated cell transfection; (e) polybrene mediated delivery; (f) protoplast fusion; (g) microinjection; and (h) polylysine mediated transformation, with the genetically engineered cells transferred back to the mammalian host.

Production of Transgenic Animals

Transgenic animals containing a mutant NOS gene, preferably a mutant eNOS or nNOS gene, as described herein are also included in the invention. Transgenic animals are genetically modified animals into which recombinant, exogenous or cloned genetic material has been experimentally transferred. Such genetic material is often referred to as a "transgene". The nucleic acid sequence of the transgene, in this case a form of NOS, may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. Nos. 4,736,866; 5,602,307; Mullins et al. (1993) Hypertension 22(4):630-633; Brenin et al. (1997) Surg. Oncol. 6(2)99-110; Tuan (ed.), *Recombinant Gene Expression Protocols*, Methods in Molecular Biology No. 62, Humana Press (1997)).

A number of recombinant or transgenic mice have been produced, including those which express an activated oncogene sequence (U.S. Pat. No. 4,736,866); express simian SV 40 T-antigen (U.S. Pat. No. 5,728,915); lack the expression of interferon regulatory factor 1 (IRF-1) (U.S. Pat. No. 5,731, 490); exhibit dopaminergic dysfunction (U.S. Pat. No. 5,723, 719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al. (1996) Genetics 143(4):1753-1760); or, are capable of generating a fully human antibody response (McCarthy (1997) The Lancet 349(9049):405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997) Mol. Reprod. Dev. 46(4):515-526; Houdebine (1995) Reprod. Nutr. Dev. 35(6): 609-617; Petters (1994) Reprod. Fertil. Dev. 6(5):643-645; Schnieke et al. (1997) Science 278(5346):2130-2133; and Amoah (1997) J. Animal Science 75(2):578-585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307. Furthermore, the production of NOS transgenic animals is well developed. For instance, transgenic mice which inducibly express or overexpress wild type eNOS have been produced (see Ohashi et al. (1998) *J. Clin. Invest.* 102(12):2061-71; and Drummond et al. (1998) *J. Clin. Invest.* 102(12):2033-4). These methods may be used to produce transgenic mice which express the NOS mutants of the invention.

Therapeutic Screening Assays

The discovery that phosphorylation of eNOS regulates its activity allows for the development of screening assays to identify agents which modulate Akt regulated NOS, preferably eNOS or nNOS, activity or expression. Any available format may be used, including in vivo transgenic animal assays, in vitro protein based assays, cell culture assays and high-throughput formats.

In many drug screening programs which test libraries of compounds, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an inhibition of, for instance, binding between molecules.

Cell or tissue culture based assays may be performed, for example, by plating COS-7 cells (100 mm dish) and transfecting with NOS (7.5-30 mg) and Akt (1 mg) plasmids using calcium phosphate. To balance all transfections, an expression vector for β-galactosidase cDNA may be cotransfected. Twenty-four to forty-eight hours after transfection, the expression of appropriate proteins (40-80 mg) may be confirmed by Western blot analysis using eNOS mAb (9D10, Zymed), HA mAb (12CA5, Boehringer Mannheim), iNOS pAb (Zymed Laboratories) or nNOS mAb (Zymed Laboratories).

Twenty-four to forty-eight hours after transfection, media may be processed for the measurement of nitrite ($NO_2^-$), the stable breakdown product of NO in aqueous solution, by NO specific chemiluminescence as described (Sessa et al., 1995). Media is deproteinized and samples containing $NO_2^-$ are refluxed in glacial acetic acid containing sodium iodide. Under these conditions, $NO_2^-$ is quantitatively reduced to NO which is quantified by a chemiluminescence detector after reaction with ozone in a NO analyzer (Sievers, Boulders, Colo.). In all experiments, controls may be prepared by inhibiting $NO_2^-$ release by the use of a NOS inhibitor. In addition, $NO_2^-$-release from cells transfected with the β-galactosidase cDNA may subtracted to control for background levels of $NO_2^-$ found in serum or media cGMP accumulation in COS may also be used as a bioassay for the production of NO as described. In an alternative format, the conversion of $^3$H-L-arginine to $^3$H-L-citrulline may be used to determined NOS activity in COS cell or endothelial cell lysates as previously described (Garcia-Cardena et al., 1998).

For in vivo phosphorylation studies, COS cells may be transfected with the cDNAs for wild-type or S635 (control), bovine 1179A, D, or E eNOS, human 1177 D or E eNOS, rat 1412D or E nNOS, human 1415D or E nNOS and HA-Akt overnight. 36 hrs after transfection, cells are placed into dialyzed serum replete, phosphate-free Dulbecco's minimum essential medium supplemented with 80 μCi/ml of $^{32}$P orthophosphoric acid for 3 hr. A cell aliquot may be pretreated with wortmannin (500 nM) in the phosphate-free media for 1 hr and during the labeling. Lysates are then harvested, NOS solubilized and partially purified by ADP sepharose affinity chromatography as previously described and the $^{32}$P incorporation into NOS visualized after SDS-PAGE (7.5%) by autoradiography and the amount of NOS protein verified by Western blotting for NOS.

For in vitro phosphorylation studies, recombinant NOS purified from *E. coli*, eNOS purified from another source, or NOS peptides spanning the Akt phosphorylation site are incubated with wild-type or kinase inactive Akt immunoprecipitated from transfected COS cells. Briefly, the NOS proteins or peptides are incubated with $^{32}$P g-ATP (2 ml, specific activity 3000 Ci/mmol), ATP (50 mM), DTT (1 mM), in a buffer containing HEPES (20 mM, pH=7.4), MnCl$_2$ (10 mM), MgCl$_2$ (10 mM) and immunoprecipitated Akt for 20 min at room temperature.

In experiments examining the in vitro phosphorylation of wild-type and mutant NOS, recombinant Akt (1 mg) purified from baculovirus infected SF9 cells, is incubated with wild-type, S1179A bovine eNOS, S1177A human eNOS, S1179 D or E bovine eNOS, S1177D or E human eNOS, S1412D or E rat nNOS, or S1415D or E human nNOS using essentially the same conditions as above. Proteins may be resolved by SDS-PAGE and $^{32}$P incorporation and the amount of protein determined by Coomassie staining as above.

The above screening assays which assay the Akt dependent phosphorylation or activation of NOS, preferably eNOS or nNOS, may be used to screen for a wide-variety of agents. For instance, agents which inhibit the dephosphorylation of NOS (phosphatase inhibitors) at an amino acid corresponding to serine 1179 in bovine eNOS, residue 1177 in human eNOS, residue 1412 in rat nNOS, or 1415 in human nNOS may be useful therapeutic molecules. Similarly, agents which activate Akt or which mimic the Akt phosphorylation site on eNOS may be useful therapeutic molecules.

Agents that are assayed in the above methods can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. For example, a rationally selected peptide agent can be a peptide whose amino acid sequence is similar to the Akt phosphorylation site in NOS, particularly, peptides or small molecules that mimic the NOS phosphorylation state.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

Use of Agents Identified as Modulating eNOS Activity

The agents of the present invention, such as agents that inhibit the dephosphorylation of NOS (phosphatase inhibitors) at an amino acid corresponding to serine 1179 in bovine eNOS, residue 1177 in human eNOS, residue 1412 in rat nNOS, or residue 1415 in human nNOS, as well as agents which activate Akt or which mimic the Akt phosphorylation site on NOS, can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. As described below, there are many methods that can readily be adapted to administer such agents.

The present invention further provides compositions containing one or more agents of the invention. While individual needs vary, a determination of optimal ranges of effective amounts of each component is within the skill of the art. Typical dosages comprise 0.1 to 100 mg/kg body wt. The preferred dosages comprise 0.1 to 10 mg/kg body wt. The most preferred dosages comprise 0.1 to 1 mg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals, such as humans, sheep, horses, cattle, pigs, dogs, cats, rats and mice, or in vitro.

The following working examples specifically point out preferred embodiments of the present invention, and are not to be construed as limiting in any way the remainder of the disclosure. Other generic configurations will be apparent to one skilled in the art.

EXAMPLES

The following procedures were employed in Examples 1-2

Cell Transfections: The bovine eNOS, human iNOS, rat nNOS cDNAs in pcDNA3 and HA-tagged wild-type Akt, Akt (K179M) or myr-Akt in pCMV6 were generated by standard cloning methods. The myr-nNOS in pcDNA3 was generated by PCR, incorporating a new amino terminus containing the eNOS N-myristoylation consensus site (MGNLKSVG, SEQ ID NO:1) fused in frame to the second amino acid of the nNOS coding sequence. In preliminary experiments in COS cells, this construct was N-myristoylated based on incorporation of $^3$H-myristic acid whereas native nNOS is not and resulted in approximately 60% of the total protein targeted into the membrane fraction of cells whereas only 5-10% of nNOS was membrane associated in COS cells. Mutation of the putative Akt phosphorylation sites in eNOS were generated using the Quick Change site-directed mutagenesis kit (Stratagene) according to the manufacturers instructions. All mutants were verified by DNA sequencing. COS-7 cells were plated (100 mm dish) and transfected with the NOS (7.5-30 mg) and Akt (1 mg) plasmids using calcium phosphate. To balance all transfections, the expression vector for β-galactosidase cDNA was used. Twenty-four to forty-eight hours after transfection, the expression of appropriate proteins (40-80 mg) were confirmed by Western blot analysis using eNOS mAb (9D10, Zymed), HA mAb (12CA5, Boehringer Mannheim), iNOS pAb (Zymed Laboratories) or nNOS mAb (Zymed Laboratories).

NO release from transfected COS cells: 24-48 hrs after transfection, media was processed for the measurement of nitrite ($NO_2^-$), the stable breakdown product of NO in aqueous solution, by NO specific chemiluminescence as described (Sessa et al., 1995). Media was deproteinized and samples containing $NO_2^-$ were refluxed in glacial acetic acid containing sodium iodide. Under these conditions, $NO_2^-$ was quantitatively reduced to NO which was quantified by a chemiluminescence detector after reaction with ozone in a NO analyzer (Sievers, Boulders, Colo.). In all experiments, $NO_2^-$ release was inhibitable by a NOS inhibitor. In addition, $NO_2^-$-release from cells transfected with the β-galactosidase cDNA was subtracted to control for background levels of $NO_2^-$ found in serum or media. In some experiments, cGMP accumulation in COS was used as a bioassay for the production of NO as described.

NOS activity assays: The conversion of $^3$H-L-arginine to $^3$H-L-citrulline was used to determine NOS activity in COS cell or endothelial cell lysates as previously described by Garcia-Cardena et al. (1998).

Phosphorylation studies in vivo and in vitro: For in vivo phosphorylation studies, COS cells were transfected with the cDNAs for wild-type or S635, 1179A eNOS and HA-Akt overnight. 36 hrs after transfection, cells were placed into dialyzed serum replete, phosphate-free Dulbecco's minimum essential medium supplemented with 80 μCi/ml of $^{32}$P orthophosphoric acid for 3 hr. Some cells were pretreated with wortmannin (500 nM) in the phosphate-free media for 1 hr and during the labeling. Lysates were harvested, eNOS solubilized and partially purified by ADP sepharose affinity chromatography as previously described and the $^{32}$P incorporation into eNOS visualized after SDS-PAGE (7.5%) by autoradiography and the amount of eNOS protein verified by Western blotting for eNOS. For in vitro phosphorylation studies, recombinant eNOS purified from E. coli was incubated with wild-type or kinase inactive Akt immunoprecipitated from transfected COS cells. eNOS was incubated with $^{32}$P g-ATP (2 ml, specific activity 3000 Ci/mmol), ATP (50 mM), DTT (1 mM), in a buffer containing HEPES (20 mM, pH=7.4), $MnCl_2$ (10 mM), $MgCl_2$ (10 mM) and immunoprecipitated Akt for 20 min at room temperature.

In experiments examining the in vitro phosphorylation of wild-type and mutant eNOS, recombinant Akt (1 mg) purified from baculovirus infected SF9 cells, was incubated with wild-type or S1179A eNOS (2.4 mg, purified from E. coli) using essentially the same conditions as above. Proteins were resolved by SDS-PAGE and $^{32}$P incorporation and the amount of protein determined by Coomassie staining as above.

In studies identifying the labeled eNOS peptide, immunoprecipitated Akt was incubated with recombinant eNOS as above. The sample was run on SDS-PAGE, and the eNOS band digested in gel, and the resultant tryptic fragments purified by RP-HPLC. Peptide mass and $^{32}$P incorporation were monitored and the prominent labeled peak further analyzed by mass spectrometry. In other experiments, peptides corresponding to the potential Akt phosphorylation site were synthesized, purified by HPLC and verified by mass spectrometry (W. M. Keck Biotechnology Resource Center, Yale University School of Medicine). The wild-type peptide was 1174RIRTQSFSLQERHLRGAVPWA1194 (SEQ ID NO:2) and the mutant peptide was identical except S1179 was changed to an alanine. In vitro kinase reactions were essentially as described above incubating peptides (25 mg) with recombinant Akt (1 mg). Reactions were then spotted onto phosphocellulose filters and the amount of phosphate incorporated measured by Cerenkov counting.

Adenoviral infections and NO release in endothelial cells: Bovine lung microvascular endothelial cells (BLMVEC) were cultured in either in 100 mm dishes (for basal NO release and NOS activity assays) or C6 well plates (for stimulated NO) as previously described (Garcia-Cardena et al., 1996a). BLMVEC were infected with 200 MOI of adenovirus containing the β-galactosidase 29, HA-tagged, inactive phosphorylation mutant Akt (AA-Akt; Alessi et al., 1996) or carboxyl terminal HA-tagged constitutively active Akt (myr-Akt) for 4 hrs. The virus was removed and cells left to recover for 18 hrs in complete medium. In preliminary experiments with the β-galactosidase virus, these conditions were optimal for infecting 100% of the cultures. For measurement of basal NO production, media was collected for NO release 24 hrs after the initial infection with virus. For measurement of stimulated NO release, cells were then washed with serum-free medium followed by stimulation with VEGF (40 ng/ml) for 30 min. In some experiments the calcium dependency of NOS was determined 24 hrs after adenoviral infection. Infected cells were lysed in NOS assay buffer containing 1% NP40, and detergent soluble material used for activity. Lysates were incubated with EGTA buffered calcium to yield appropriate amounts of free calcium in the incubation.

Statistics: Data are expressed as mean±SEM. Comparison's were made using a two-tailed, Student's t-test or ANOVA with a post-hoc test where appropriate. Differences were considered to be significant at p<0.05.

Example 1

Akt Modulates NO Production from eNOS

Figure 1B:
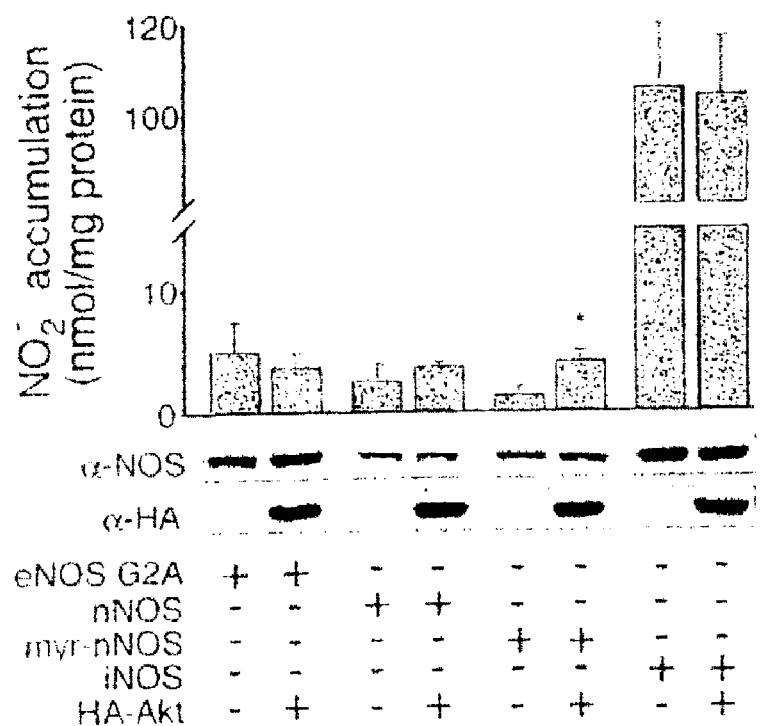

To explore the possibility that a downstream effector of PI-3 kinase, Akt, could directly influence the production of NO, COS-7 cells (which do not express NOS) were co-transfected with eNOS and wild type Akt (HA-Akt), or kinase inactive Akt (HA-Akt K179M) and the accumulation of nitrite ($NO_2^-$) measured by NO specific chemiluminescence. Transfection of eNOS results in an increase in $NO_2^-$ accumulation, an effect that is markedly enhanced by co-transfection of wild-type Akt, but not the kinase inactive variant (FIG. 1A). Identical results were obtained using cGMP as a bioassay for biologically active NO. Under these experimental conditions, Akt was catalytically active as determined by Western blotting with a phospho-Akt specific Ab (which recognizes serine 473; not shown) and Akt activity assays (see FIG. 2A). Transfection of a constitutively active form of Akt (myr-Akt) increases cGMP accumulation (assayed in COS cells) from 5.5±0.8 to 11.6±0.9 pmol cGMP/mg protein (in cells transfected with eNOS alone or eNOS with myr-Akt, respectively) whereas the kinase inactive Akt did not influence cGMP accumulation (5.8±0.8 µmol cGMP, n=4 experiments). As seen in the inset, equal levels of eNOS and Akt were expressed in COS cell lysates suggesting that Akt modulates eNOS thereby increasing NO production under basal conditions.

eNOS is a dually acylated peripheral membrane protein that targets into the Golgi region and plasma membrane of endothelial cells (Liu et al., 1997; Garcia-Cardena et al., 1996a; Shaal et al., 1996) and compartmentalization is required for efficient production of NO in response to agonist challenge (Sessa et al., 1995; Liu et al., 1996; Kantor et al., 1996). To examine if eNOS activation by Akt requires membrane compartmentalization, COS-7 cells were co-transfected with cDNAs for Akt and a myristoylation, palmitoylation defective mutant of eNOS (G2A eNOS) and the release of NO quantified. As seen in FIG. 1B, Akt did not activate the non-acylated form of eNOS suggesting that compartmentalization of both proteins to the membrane is required for their functional interaction (Downward et al., 1998). Next, it was determined if Akt could activate structurally similar but distinct soluble NOS isoforms, neuronal and inducible NOS (nNOS and iNOS, respectively). Co-transfection of Akt with nNOS and iNOS did not result in a further increase in NO release demonstrating the specificity of Akt for eNOS. However, the addition of an N-myristoylation site to nNOS, in order to enhance its interactions with biological membranes, results in Akt stimulation of nNOS in a manner analogous to that seen with eNOS, suggesting that both isoforms may be susceptible to activation by Akt kinase when membrane anchored.

Example 2

Production of eNOS Mutations

Figure 2A:
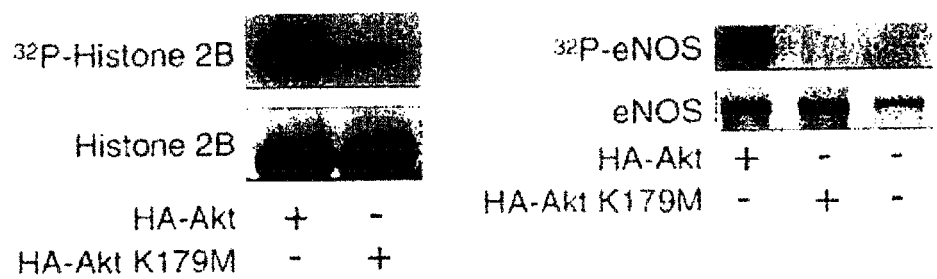
Figure 2B:
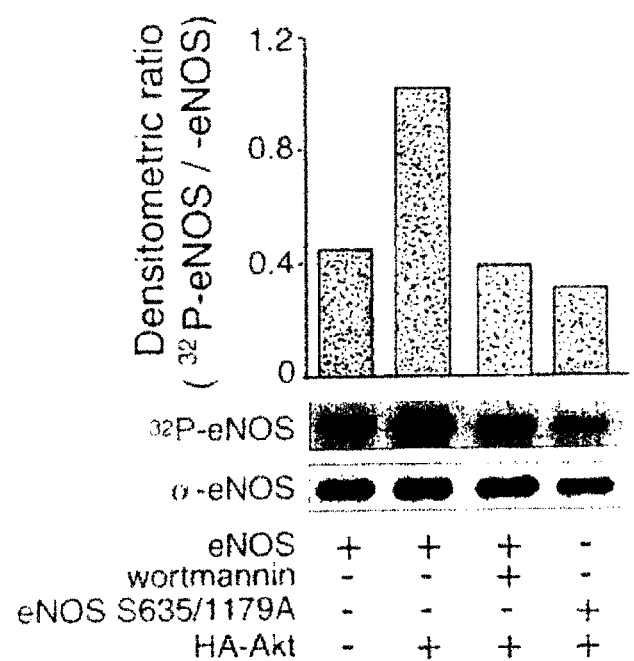

The above experiments imply that Akt, perhaps via phosphorylation of eNOS, can modulate NO release from intact cells. Indeed, two putative Akt phosphorylation motifs (RXRXXS/T) are present in eNOS (serines 635 and 1179 in bovine eNOS or serines 633 and 1177 in human eNOS) and one motif present in nNOS (serines 1412 in rat and 1415 human nNOS), with no obvious motifs found in iNOS. To examine if eNOS is a potential substrate for Akt phosphorylation in vitro, COS cells were transfected with HA-Akt or HA-Akt (K179M) and kinase activity assessed using recombinant eNOS as a substrate. As seen in FIG. 2A, the active kinase phosphorylates histone 2B and eNOS (69.3±2.9 and 115.4±3.8 pmol of ATP/nmol substrate, respectively, n=3), whereas the inactive Akt did not significantly increase histone or eNOS phosphorylation. To elucidate if the putative Akt phosphorylation sites in eNOS were responsible for the incorporation of $^{32}P$, the two serines were mutated to alanine residues and the ability of Akt to stimulate wild-type and mutant eNOS phosphorylation examined in intact COS cells. Transfected cells were labeled with $^{32}P$-orthophosphate, eNOS partially purified by ADP-sepharose affinity chromatography, and the phosphorylation state and protein levels quantified. As seen in FIG. 2B, co-expression of Akt results in a 2 fold enhancement in the phosphorylation of eNOS relative to non-stimulated cells. Pretreatment of eNOS/Akt transfected cells with wortmannin abolished the Akt induced increase in phosphorylation. Moreover, mutation of serines 635 and 1179 to alanine residues abolished Akt dependent phosphorylation of eNOS suggesting that these residues could serve as potential phosphorylation sites in intact cells.

Figure 2D:
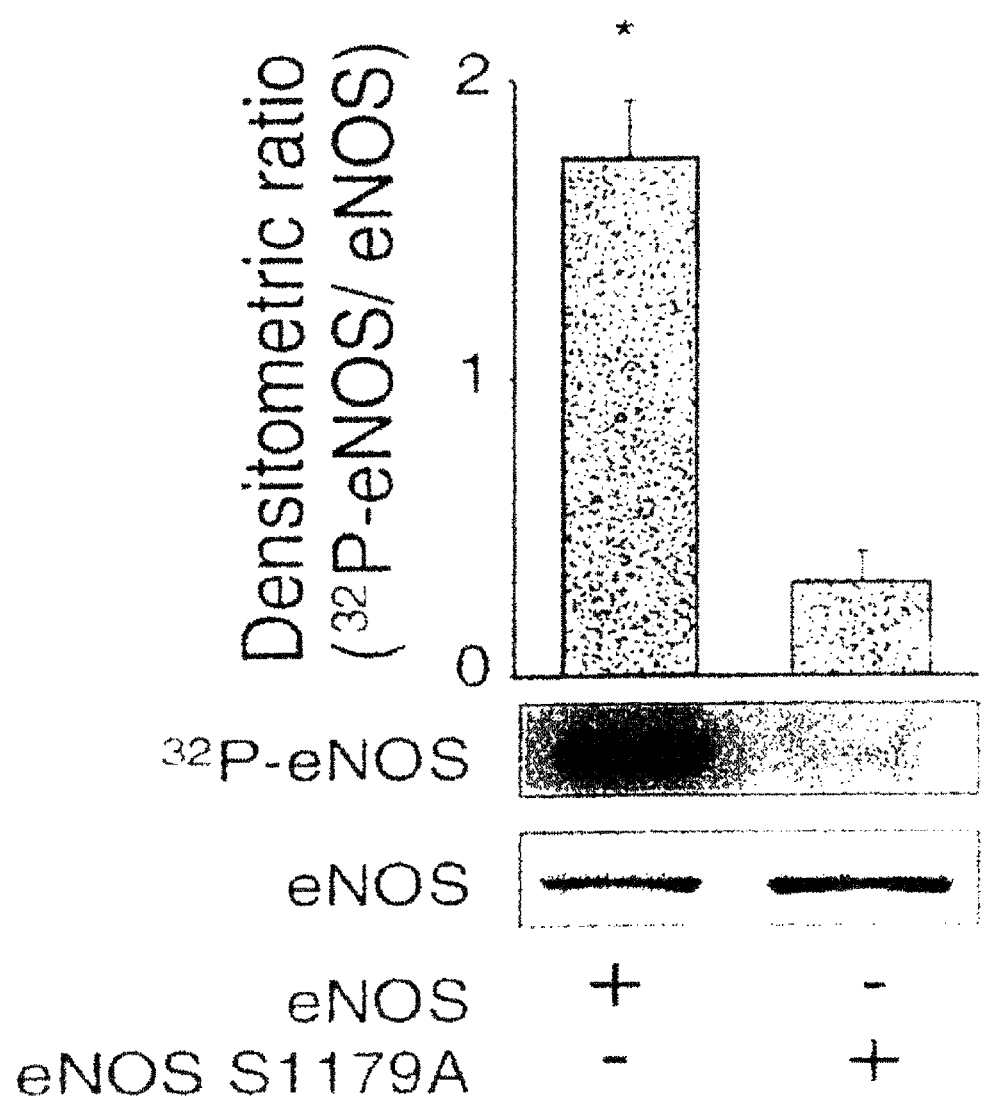

To directly identify the residues phosphorylated by Akt, wild-type eNOS was incubated with immunopurified Akt and the sites of phosphorylation determined by HPLC followed by MALDi-mass spectrometry (MALDi-MS). As seen in FIG. 2C, the primary $^{32}P$-labeled tryptic phosphopeptide co-elutes with a synthetic phosphopeptide (amino acids 1177-1185 with phosphoserine at position 1179) and has the identical mass ion as determined by linear mode MS. Using reflectron mode MALDi-MS monitoring, both the labeled tryptic peptide and the standard phosphopeptide demonstrated a loss of $HP_3O_4$ indicating that the tryptic peptide was phosphorylated. In addition, mutation of S1179 to A markedly reduces Akt-dependent phosphorylation of eNOS compared to the wild-type protein (FIG. 2D). Identical results were obtained utilizing peptides (amino acids 1174-1194) derived from wild-type or eNOS S1179A as substrates for recombinant Akt (wild-type peptide incorporated 24.6±3.7 nmol phosphate/mg compared to the alanine mutant peptide which incorporated 0.22±0.02 nmol phosphate/mg; n=5). Collectively, these data demonstrate that eNOS is a substrate for Akt and that the primary site of phosphorylation is serine 1179 (serine 1177 in human eNOS).

Figure 3:
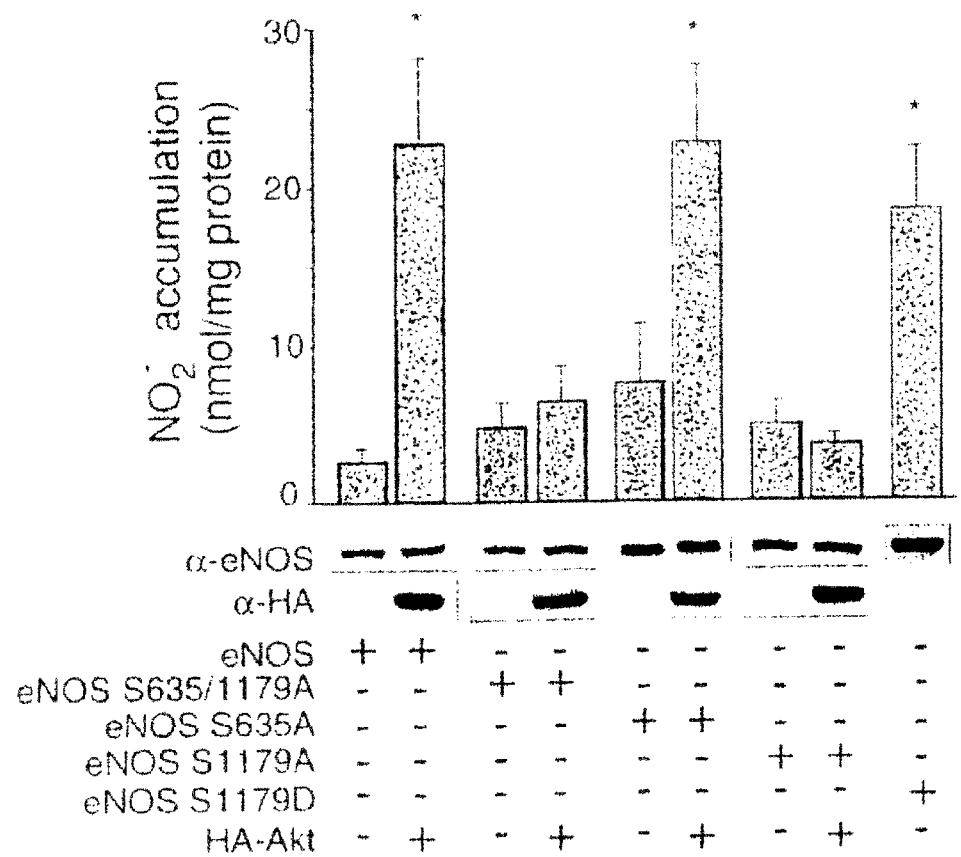
FIG. 3. Evidence that serine 1179 is functionally important for Akt stimulated NO release. COS cells were transfected with plasmids for wild-type eNOS or eNOS mutants, in the absence or presence of Akt and the expression of the proteins and production of NO (assayed as $NO_2^-$) determined. Interestingly, constructs with the S1179 mutation to A were not activated by Akt and mutation of S1179 to D resulted in a gain of function. In A, data are mean±SEM of 4-7 experiments; * represent significant differences (p<0.05).

Next we examined the functional significance of the putative Akt phosphorylation site at serine 635 and the identified site at serine 1179. Transfection of COS cells with the double mutant eNOS S635/1179A abolishes Akt dependent NO release. Mutation of serine 635 to alanine did not attenuate NO release whereas eNOS S1179A abolishes Akt dependent activation of eNOS (FIG. 3). These results suggest that serine 1179 is functionally important for NO release. Mutation of serine 1179 into aspartic acid (eNOS S1179D) to substitute for the negative charge afforded by the addition of phosphate, partially mimics the activation state induced by Akt (S1177D in human eNOS). All site directed mutants were amply expressed (see inset Western blots) and retained NOS catalytic activity in cell lysates (in COS cells transfected with eNOS only, NOS activity was 85.3±27.0, 71.9±2.9, 80.8±23.2 and 131.8±36.7 pmol L-citrulline generated/mg protein from lysates of COS cells expressing wild type, S1179A, S635, 1179A and eNOS S1179D, respectively, n=3 experiments).

Figure 4A:
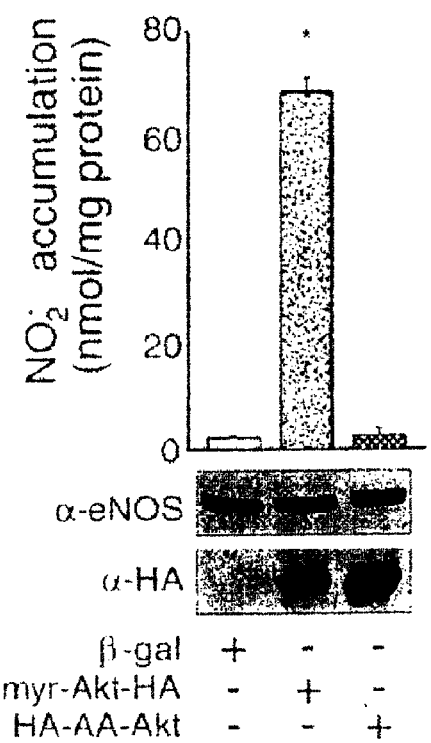
FIGS. 4A-4C. Akt regulates the basal and stimulated production of NO in endothelial cells.
Figure 4B:
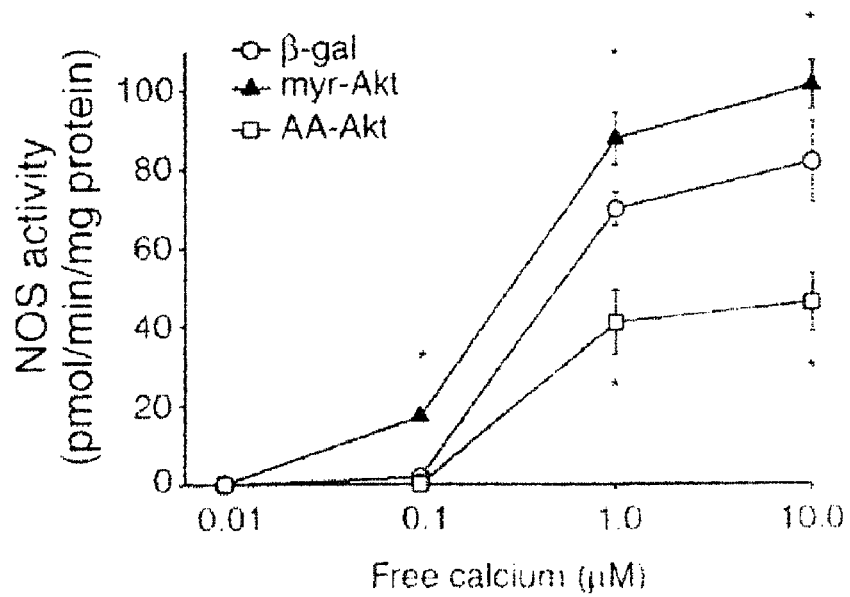

To examine if Akt mediates NO release from endothelial cells, bovine lung microvascular endothelial cells (BLM-VEC) were infected with adenoviruses expressing activated Akt (myr-Akt), activation deficient Akt (AA-Akt) or β-galactosidase as a control and the accumulation of NO measured. As seen in FIG. 4A, myr-Akt stimulates the basal production of NO from BLMVEC, whereas cells infected with β-galactosidase or activation deficient Akt released low levels of NO that were close to the limits of detection. These data in conjunction with similar results in COS cells suggests that Akt phosphorylation of eNOS is sufficient to regulate NO production at resting levels of calcium. Indeed, NOS activity measured in lysates from myr-Akt infected BLMVEC demonstrates that the sensitivity of the enzyme to activation by calcium, assayed at a fixed calmodulin concentration, is enhanced relative to NOS activity seen in BLMVEC infected with the β-galactosidase virus (FIG. 4B). Interestingly, the calcium sensitivity of NOS activity in cells infected with activation deficient Akt was greatly suppressed relative to both myr-Akt and β-galactosidase infected cells.

Figure 4C:
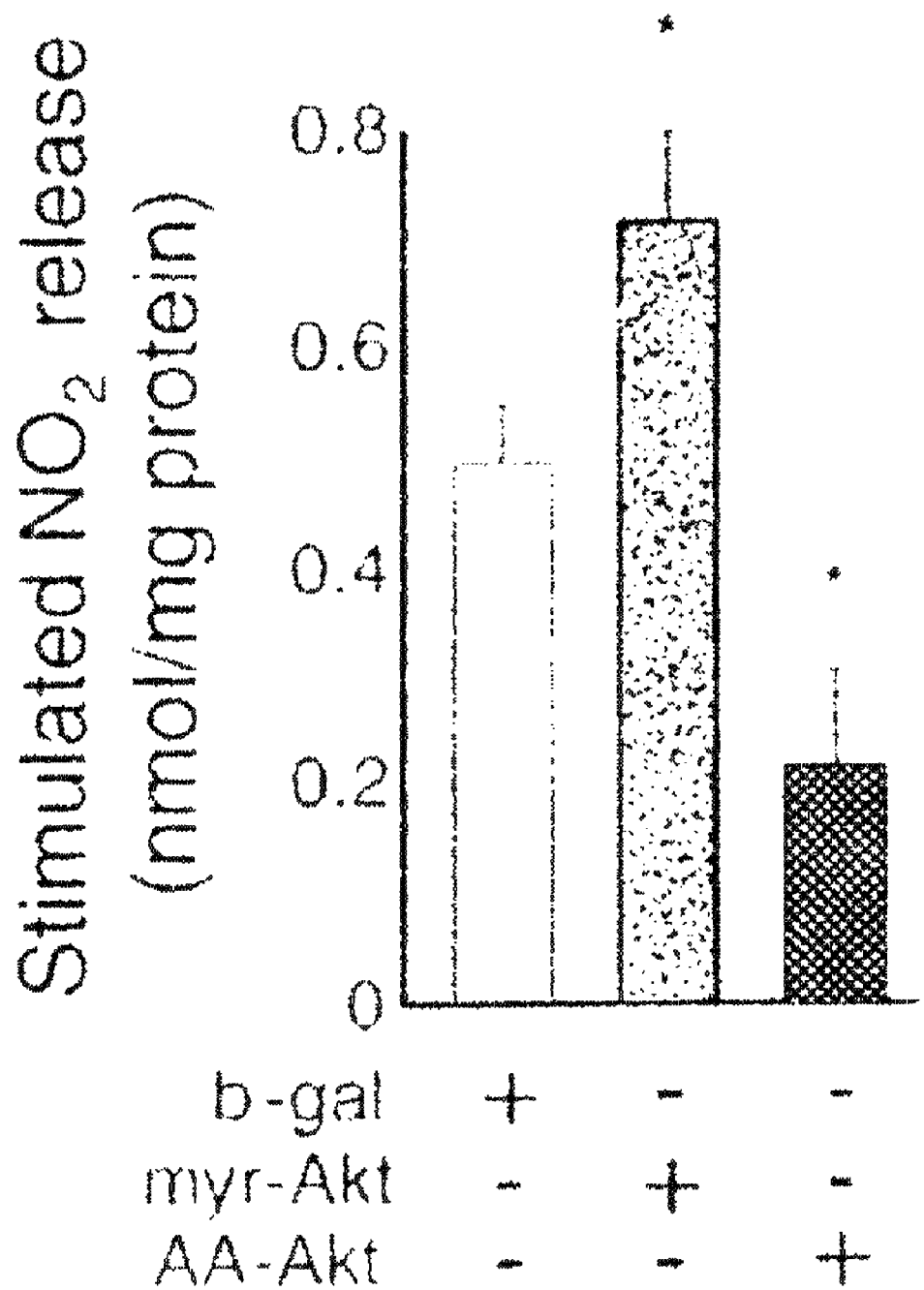

Treatment of endothelial cells with VEGF is known to activate Akt 23 and the release of NO through a mechanism partially blocked by inhibitors of PI-3 kinase (Papapetropoulos et al., 1997). To examine the functional link between VEGF as an agonist for NO release and Akt activation, BLMVEC were infected with adenoviruses for myr-Akt, AA-Akt or β-galactosidase and VEGF stimulated NO release quantified. As seen in FIG. 4C, infection of endothelial cells with myr-Akt enhances VEGF driven NO production while the AA-Akt attenuates NO release. These results imply that Akt participates in the signal transduction events required for both basal and stimulated NO production in endothelial cells.

Collectively these data demonstrate that Akt can phosphorylate eNOS on serine 1179 (serine 1177 in human eNOS) and that phosphorylation enhances the ability of the enzyme to generate NO.

Example 3

Materials and Methods eNOS Constructs and Protein Purification—Wild type bovine eNOS in the plasmid pCW was expressed as described previously with groELS in *E. coli* BL21 cells (Martasek et al., 1996). The S1179D mutant eNOS for expression in *E. coli* was generated as follows. eNOS S1179D in pcDNA 3 (Fulton et al., 1999) was digested with XhoI/XbaI, subcloned into the identical sites of eNOS in pCW, and co-expressed with groELS. Isolation of recombinant eNOS was preformed as reported previously (Roman et al., 1995; Martasek et al., 1999), with the following modifications. eNOS was eluted from 2'5'-ADP Sepharose with either 10 mM NADPH or 10 mM 2'-AMP. The amount of eNOS was quantitated using the peak absorbance at 409-412 nm, with an extinction coefficient for heme content of 0.1 $\mu M^{-1}$ $cm^{-1}$. The purity of eNOS was determined by 7.5% SDS-PAGE followed by Coomassie staining. Low temperature SDS-PAGE was performed identically, except that samples were not boiled and the electrophoresis was carried out at 4° C. in a slurry of ice/water (Klatt et al., 1995). In experiments in which NOS cofactors (L-arginine, calmodulin, and NADPH) were titrated, they were omitted from the purification and storage of the enzymes and were incubated as described below.

Assay for NOS Activity—NO production was measured by the hemoglobin capture assay as described (Kelm et al., 1988). Briefly, the reaction mixture contained eNOS (0.5-2.5 μg), oxyhemoglobin (8 μM), L-arginine (100 μM), BH4 (5 μM), CaCl2 (120 μM), calmodulin (120-200 nM), and NADPH (100 μM) in HEPES buffer (50 mM), pH 7.4. In the determination of calcium EC50 value for eNOS, the above reaction mixture was modified as follows: MOPS buffer (10 mM, pH 7.6), KCl (100 mM) and CaM (250 nM) were substituted. Under these conditions, free calcium was calculated using the WinMAXC program, version 1.8 (Stanford University), with a Kd of $2.2 \times 10^{-8}$ M. The precise free calcium concentration was achieved by mixing an appropriate proportion of 10 mM $K_2$EGTA and 10 mM CaEGTA stock solutions (Molecular Probes). NOS activity was monitored for linearity over 2 min at 401 nm, and NO production was calculated based on the change of absorbance using the extinction coefficient of 60 $mM^{-1}$ $cm^{-1}$. All reactions were carried out at 23° C., and each data point represents 3-8 observations. The extinction coefficient of 0.0033 $\mu M^{-1}$ $cm^{-1}$ at 276 nm was used for determination of calmodulin concentration. The production of NO using this method was completely blocked by the addition of nitro-L-arginine (1 mM). When the inactivation of eNOS was determined by the addition of EGTA (200-800 μM) to the reaction mixture, chelator was added 1 min after initiation of the reaction by NADPH. Identical conditions were used when NADPH-cytochrome c reductase activity was examined. These reactions contained CaM (120 nM) and CaCl2 (200 μM) in a 0.5-ml volume with eNOS (0.5 μg).

The conversion of L-arginine to L-citrulline was assayed as described previously by Bredt et al. (1990). Briefly, eNOS (0.25-2 μg) was incubated for 3-10 min at 23° C. in the following reaction mixture: 3 pmol of L-[3H]arginine (55 Ci/mmol), 10-300 μM arginine, 1 mM NADPH, 120-200 nM calmodulin, 2 mM CaCl2, and 30 μM BH4 in a final reaction volume of 50-100 μl. The reaction was terminated by the addition of 0.5 ml of 20 mM HEPES, pH 5.5, containing 2 mM EGTA and EDTA. The reaction mixture was placed over Dowex AG50WX8, and the flow-through was counted on a Packard 1500 liquid scintillation analyzer.

Assays for Reductase Activity—NADPH-cytochrome c reductase activity and 2,6-dichlorophenolindophenol (DCIP) reduction were measured as a change in absorbance at 550 nm as described previously by Martasek et al. (1999) and Masters et al. (1967) using an extinction coefficient of 0.021 $\mu M^{-1}$ $cm^{-1}$ for both cytochrome c and DCIP. Briefly, a reaction mixture (1 ml) contained either cytochrome c (90 μM); DCIP (36 μM), HEPES buffer (50 mM) at pH 7.6, NaCl (250 mM), NADPH (100 μM), calmodulin (120 nM), and CaCl2 (200 μM); or other substances as indicated. The reaction was monitored for 60 s (at 23° C.) after the addition of eNOS. When inactivation of reductase activity was determined by the addition of EGTA (200-800 μM), chelator was added 1 min after initiation of the reaction and monitored for an additional 1 min. The reaction contained HEPES buffer (50 mM) at pH 7.6, CaM (120 nM), and CaCl2 (200 μM) and was initiated with NADPH (100 μM). No NaCl was added in experiments that examined EGTA inactivation of eNOS to mimic the conditions used in the hemoglobin capture experiments. The addition of NOS inhibitors did not influence the rate of cytochrome c reduction (not shown). Determination of the calcium EC50 for eNOS was performed as described above for the hemoglobin capture assay.

Data Analysis and Statistics—All data were expressed as mean±S.E. At least triplicate determinations were performed with a minimum of three different batches of enzymes for each data set. Wild type and mutant enzymes were purified simultaneously to control for activity variations between preparations. Statistical significance was determined using Student's t test, and p<0.05 was considered statistically significant.

Results

Figure 6A:
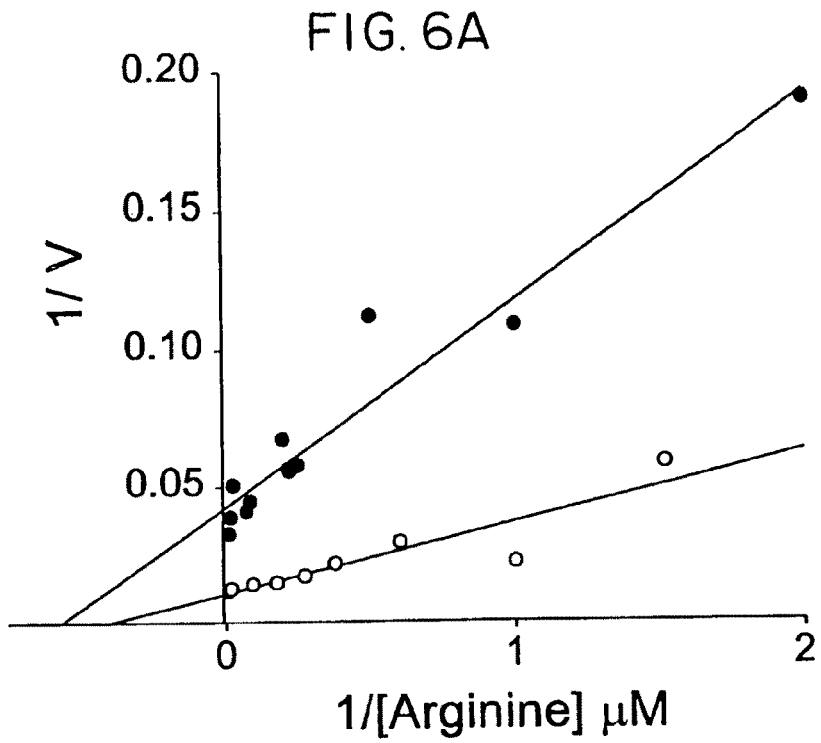
FIGS. 6A and 6B. eNOS S1179D has higher rates of NO production (A) and reductase activity (B) than does wild type eNOS. In A, the rate of NO generated from wild type (●) and S1179D (○) eNOS was determined, using the hemoglobin capture assay, as a function of L-arginine concentration, and data are presented in a double reciprocal plot. In B, DCIP and cytochrome c assays were performed in the presence or absence of CaM. Values are mean±S.E., n=4-6 determinations. Similar results were obtained with at least three enzyme preparations. Significant differences (p<0.05) between the wild type and S1179D eNOS are indicated by the asterisks.

Expression and Purification of eNOS—Both wild type and S1179D eNOS were expressed and purified from *E. coli*. In a culture of 1.6 liters, approximately 2.5-4.0 mg of eNOS was typically recovered using 2'5'-ADP Sepharose 4B chromatography. As seen in FIG. 5A, both enzymes were >90% pure based on Coomassie staining. These results are typical, as seen from seven independent preparations of both wild type and S1179D eNOS prepared side-by-side. Both enzymes were primarily in their dimeric form, as shown by low temperature SDS-PAGE (FIG. 5B).

eNOS S1179D Has Greater NO Synthase and Reductase Activities Than Does Wild Type eNOS—Next, the activities of wild type and S1179D eNOS were compared by measuring the rate of NO production. S1179D eNOS exhibited a higher turnover number (under optimal conditions) as compared with wild type enzyme (84±6 versus 27±1 $min^{-1}$, n=6 separate and paired preparations of enzymes). The Km values with L-arginine were similar for wild type and S1179D eNOS (FIG. 6A, 1.8 versus 2.5 μM, respectively; see Table I).

with both enzymes (30% for wild type and 22% for S1179D eNOS), suggesting that the enhanced reductase activity of S1179D compared with wild type eNOS (assayed by cytochrome c reduction) was not due to uncoupling of the enzyme.

NADPH-dependent NO Formation and Reductase Activities Are Not Different for Wild Type and S1179D eNOS—The NADPH dependence of NO production and cytochrome c reduction were examined because the NADPH binding site lies close in proximity to the Ser-1179 in eNOS. S1179D eNOS had a higher maximum turnover number ($k_{cat}$) than did

TABLE I

Kinetic parameters for wild type and S1179D eNOS

| | | cofactors | | |
|---|---|---|---|---|
| Substrate | Assay | Catalytic determination | Wild type | S1179D |
| Arginine | Hemoglobin capture | $K_{cat}$ | 27 ± 1 $min^{-1}$ | 84 ± 6 $min^{-1}$ |
| | | $K_m$ | 1.8 μM | 2.5 μM |
| | Hemoglobin capture | $K_{cat}$ | 17 ± 1 $min^{-1}$ | 53 ± 3 $min^{-1}$ |
| | | $K_m$ | 8 μM | 36 μM |
| | Cytochrome c | $K_{cat}$ + CaM | 460 ± 18 $min^{-1}$ | 840 ± 59 $min^{-1}$ |
| | | $K_{cat}$ − CaM | 70 ± 5 $min^{-1}$ | 290 ± 9 $min^{-1}$ |
| | | $K_m$ + CaM − | 0.75 μM | 1.9 μM |
| NADPH | | CaM | 0.40 μM | 2.0 μM |
| | L-Citrulline | $K_{cat}$ | 22 ± 2 $min^{-1}$ | 43 ± 2 $min^{-1}$ |
| | | $EC_{50}$ | 8 nM | 7 nM |
| | Cytochrome c | $K_{cat}$ | 620 ± 78 $min^{-1}$ | 1140 ± 75 $min^{-1}$ |
| CaM | | $EC_{50}$ | 13 nM | 21 nM |
| | Hemoglobin capture | $K_{cat}$ | 58 ± 1 $min^{-1}$ | 100 ± 3 $min^{-1}$ |
| | (100 mM KCl) | $EC_{50}$ | 310 nM | 250 nM |
| | Cytochrome c | $K_{cat}$ | 1909 ± 33 $min^{-1}$ | 3798 ± 54 $min^{-1}$ |
| Ca2+ | (100 mM KCl) | $EC_{50}$ | 290 nM | 220 nM |

Figure 6B:
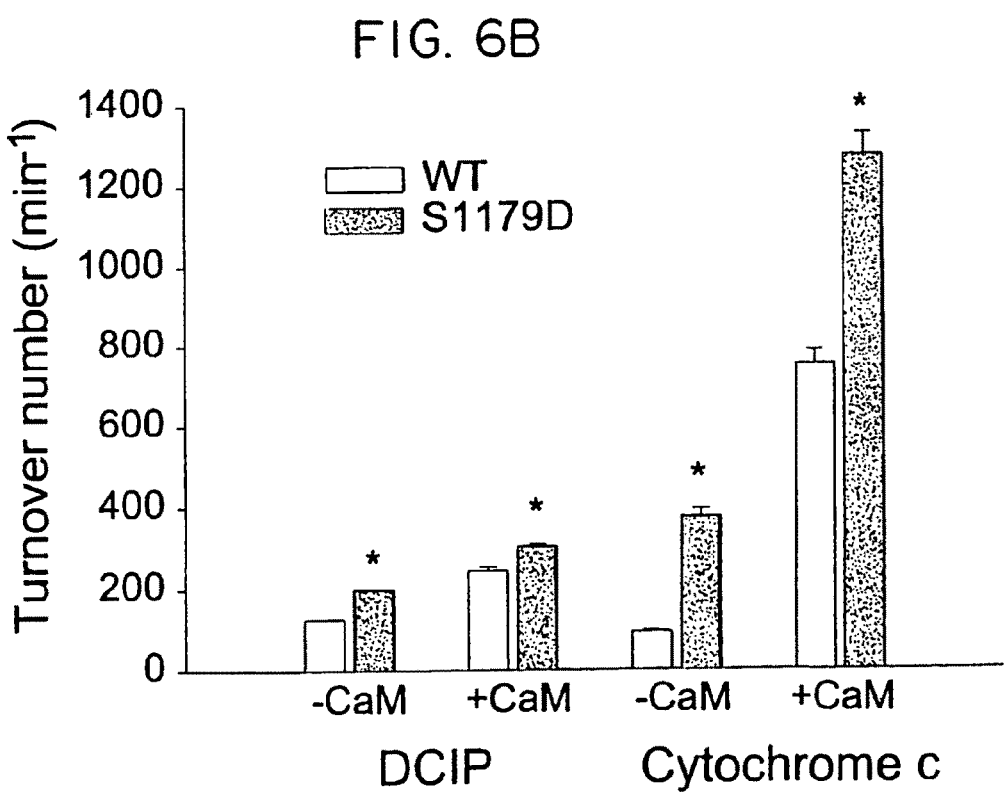

Because the rate of electron flux from the reductase domain to the oxygenase domain is critical for NOS catalysis, the increase in S1179D eNOS activity was examined to determine whether it could be attributed to enhanced reductase activity. When both DCIP and cytochrome c reduction were examined, a significant increase in activity for S1179D compared with wild type eNOS was observed (FIG. 6B). Furthermore, this increase was accentuated by the presence of CaM, which increased the overall activity for both enzymes. Basal cytochrome c reduction, in the absence of CaM, was 4-fold higher for S1179D compared with wild type eNOS. The magnitude of CaM-stimulated cytochrome c reduction was higher for S1179D eNOS (749±35 versus 1272±55 $min^{-1}$ for wild type and S1179D eNOS, respectively, n=3-5); however, the level of stimulation by CaM was 8-fold for wild type eNOS compared with only 3-fold for S1179D eNOS.

Figure 7A:
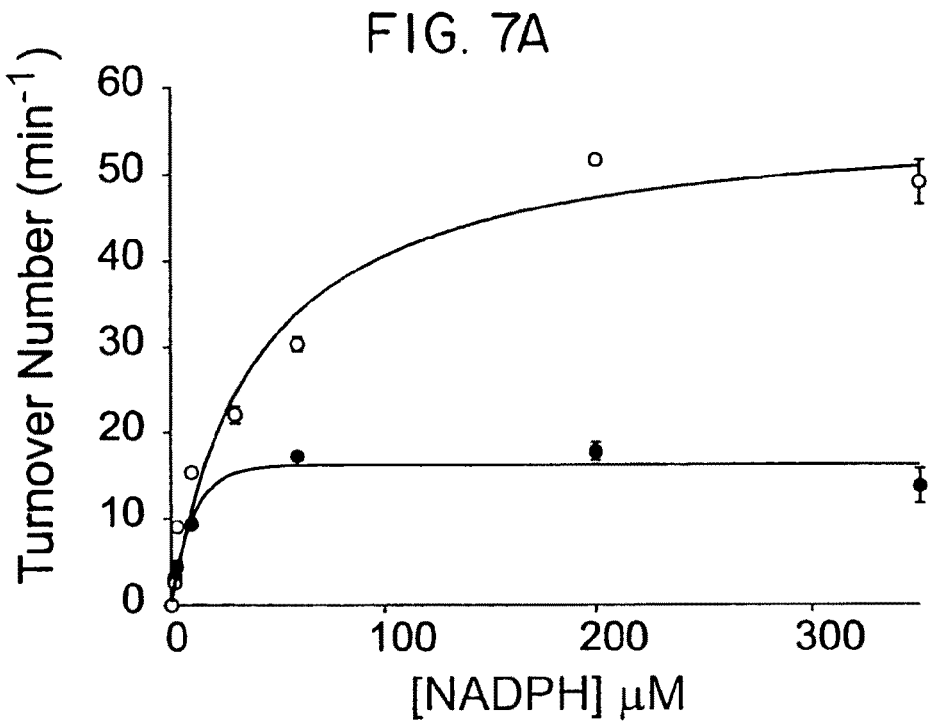
FIGS. 7A and 7B. NOS activities (A) and NADPH-dependent reductase (B) are increased with eNOS S1179D compared with the wild type enzyme. Hemoglobin capture (A) and NADPH-dependent cytochrome c reduction (B) assays were performed on both wild type and S1179D eNOS. In A, the rate of NO production was determined in the presence of all NOS cofactors (wild type (filled symbols) and S1179D (open symbols) eNOS). The rate of cytochrome c reduction was performed in the absence of arginine and BH4 (A) for wild type (circles) and S1179D (triangles) in the presence (filled symbols) or absence of 120 nM calmodulin (open symbols). Values are mean±S.E., n=3-6 determinations from at least three enzyme preparations.
Figure 7B:
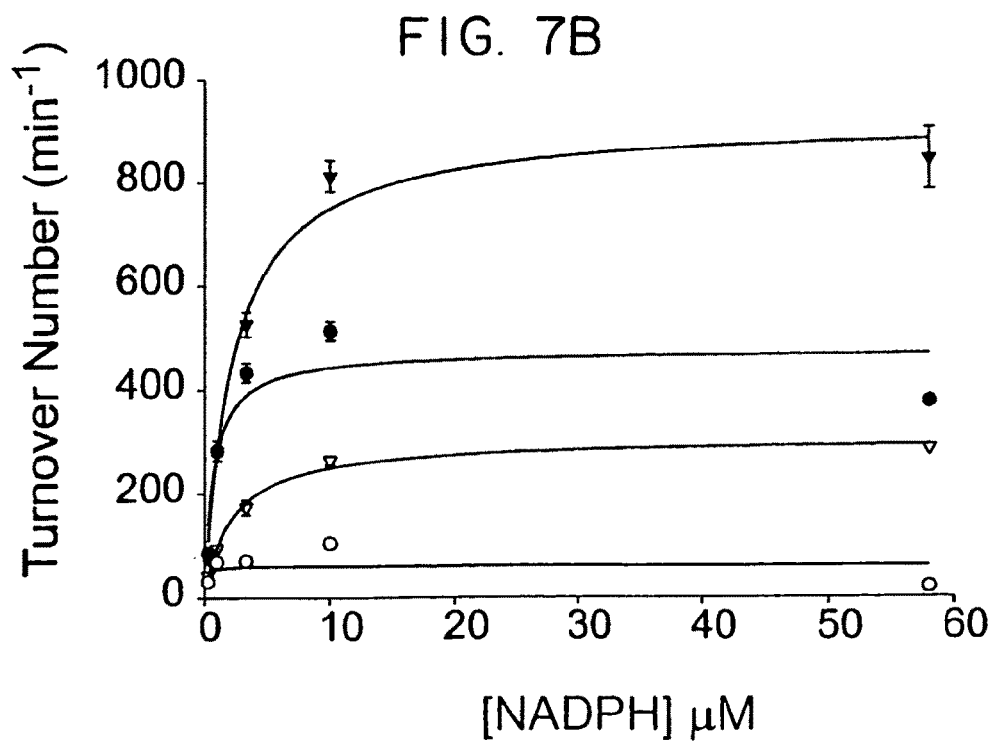

Next, it was determined whether S1179D eNOS produces more superoxide than wild type eNOS, which could reduce cytochrome c. As expected, no superoxide dismutase inhibitable cytochrome c reduction was observed (as an index of superoxide anion generation) in the absence of CaM, as reported earlier for wild type eNOS (86±6 versus 95±8 $min^{-1}$) and for S1179D eNOS (278±9 versus 288±7 $min^{-1}$, n=3-5). However, in the presence of CaM, superoxide dismutase reduced the rate of cytochrome c reduction for both wild type (610±51 versus 866±8 $min^{-1}$) and S1179D (1179±43 versus 1518±19 $min^{-1}$) eNOS. The relative decrease in cytochrome c activity in the presence of superoxide dismutase was similar wild type enzyme based on NO production, assayed in the presence of CaM (FIG. 7A). The increased $k_{cat}$ was associated with a 4-fold increase in the Km for NADPH for S1179D eNOS compared with wild type eNOS (36 versus 8 μM, respectively). The $k_{cat}$ for NADPH-dependent cytochrome c reduction in the absence of CaM was greater for eNOS S1179D than wild type eNOS (290 versus 70 $min^{-1}$, respectively; FIG. 7B). In the presence of CaM, the $k_{cat}$ for cytochrome c reduction was considerably higher for S1179D compared with wild type eNOS (840 versus 460 $min^{-1}$, respectively). The Km values for NADPH were unchanged in the absence or presence of CaM (0.40 and 0.75 μM for wild type eNOS and 2.0 and 1.9 μM for S1179D eNOS in the absence and presence of CaM, respectively).

Figure 8A:
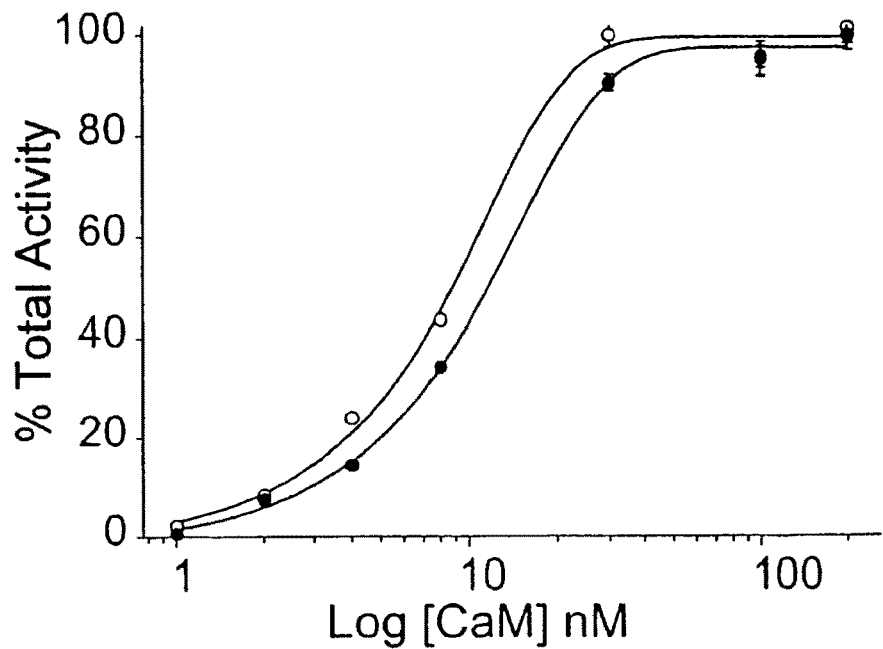
FIGS. 8A-8D. Calmodulin- and calcium-dependent activation of NOS and reductase activities are slightly enhanced for S1179D eNOS. Calmodulin-dependent hemoglobin capture (A) and cytochrome c reduction (B) were performed on both wild type (filled symbols) and S1179D eNOS (open symbols). The rate of NO production detected by hemoglobin capture method is in the presence of all NOS cofactors, whereas cytochrome c reduction was performed in the absence of arginine and BH4. In C and D, identical experiments were performed in the presence of increasing concentrations of free calcium. The insets in C and D depict the calcium-dependent turnover of S1179D and wild type eNOS in both NO production and cytochrome c assays. The maximal turnover rates were as follows for wild type and S1179D eNOS, respectively: A, 22 and 43 min$^{-1}$; B, 620 and 1400 min1; C, 58 and 100 min1; and D, 1930 and 3810 min$^{-1}$. Values are mean±S.E., n=3-6 determinations from at least three enzyme preparations.
Figure 8B:
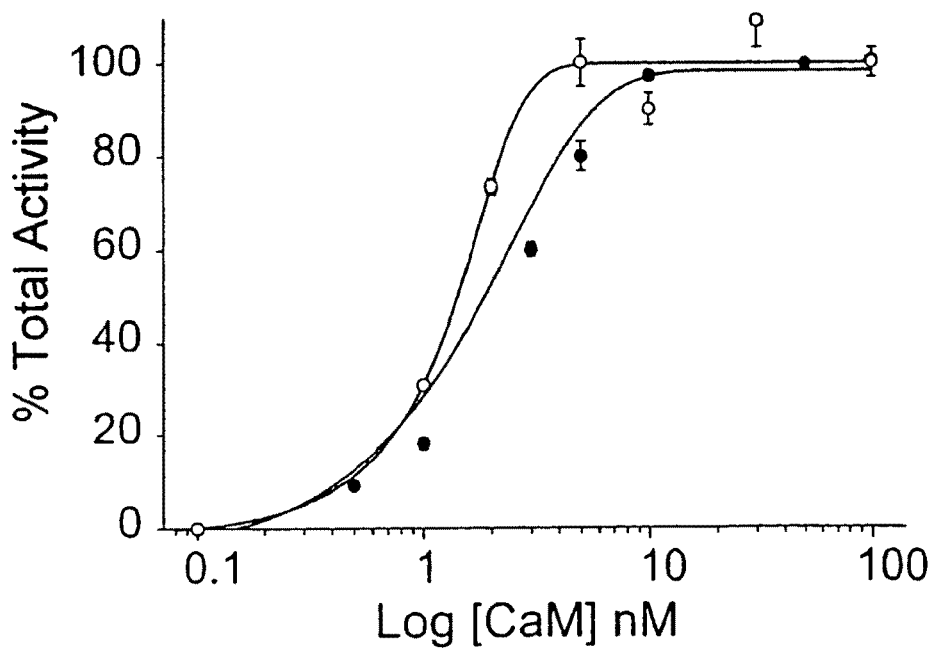

EC50 Values for CaM Are Unchanged between Wild Type and S1179D eNOS—To assess whether the increased activity of S1179D eNOS was attributable to changes in the affinity of the enzyme for CaM, the kinetics of NOS activity and cytochrome c reduction assayed in the presence of all NOS cofactors in excess as a function of CaM concentration were examined. The kcat for CaM activation of NOS activity was 22 $min^{-1}$ for wild type and 43 $min^{-1}$ for S1179D eNOS. Transformation of the data, normalizing for the differences in $k_{cat}$, revealed a slight shift in the curve to the left for S1179D eNOS but little difference in the EC50 values for CaM, consistent with reported data on phospho-eNOS (Mitchell et al., 1999). The EC50 values were 8 nM for wild type and 7 nM S1179D eNOS (FIG. 8A). NADPH-mediated cytochrome c reduction was measured. The $k_{cat}$ for CaM activation of cytochrome c reduction was about 2-fold higher for S1179D eNOS compared with wild type enzyme (1140 and 620 min$^{-1}$ for S1179D and wild type eNOS, respectively). Transformation of the data normalized for the differences in $k_{cat}$, revealed small differences in the EC50 values for CaM between wild type and S1179D eNOS (21 versus 13 nM; FIG. 8B).

Figure 8C:
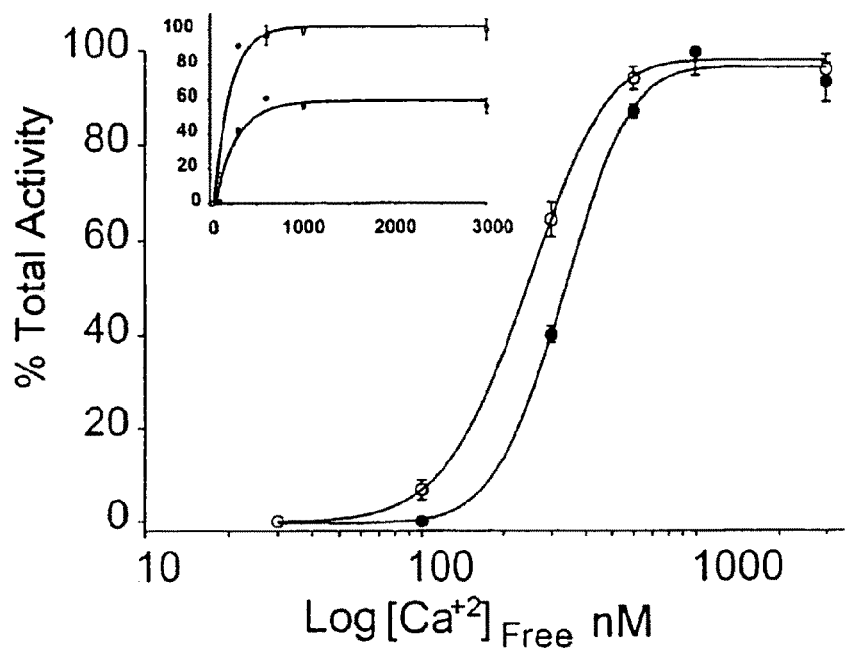
Figure 8D:
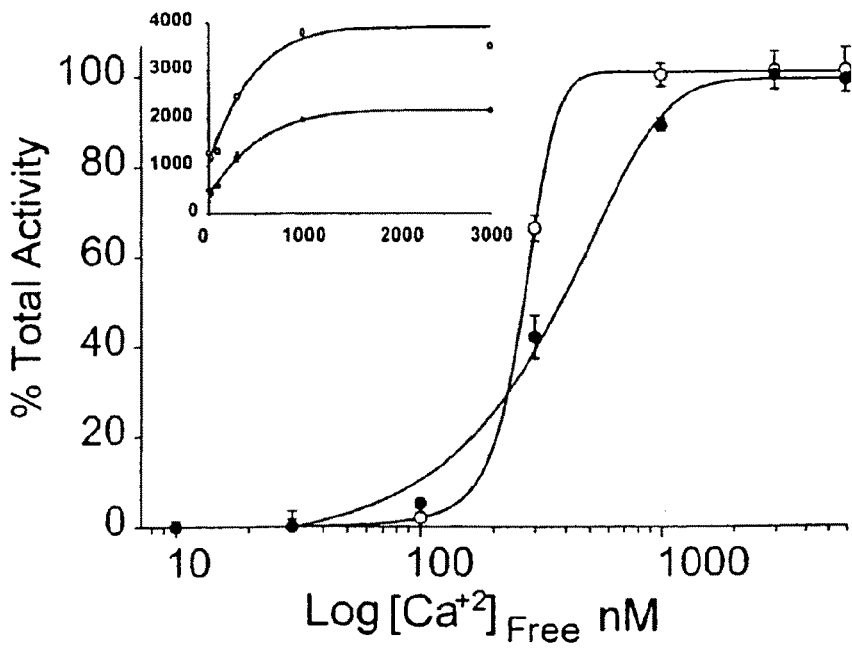

Comparison of Calcium Activation and Inactivation of eNOS—In previous experiments, it was demonstrated that the "apparent calcium sensitivity" of eNOS was enhanced in cells expressing either a majority of phospho-eNOS or S1179D eNOS, suggesting that phosphorylation changed the affinity of calcium/CaM activation (Dimmeler et al., 1999; Fulton et al. 1999). As seen in FIG. 8C, after normalization for the differences in maximal activity, the calcium dependence was slightly increased for S1179D eNOS ($p<0.05$, two-way analysis of variance). The EC50 values for calcium with wild type and S1179D eNOS were slightly different also (310 and 250 nM calcium, respectively), as determined by NO production (in the presence of 250 nM CaM). As seen in the inset to FIG. 8C, increasing concentrations of free calcium did indeed enhance S1179D eNOS turnover to a greater extent then that seen with wild type enzyme. Furthermore, the EC50 value for calcium assaying cytochrome c reduction were similar to those obtained measuring NO production (FIG. 8D; 290 and 220 nM for wild type and S1179D eNOS, respectively). Again, the Vmax for calcium activation of S1179D eNOS turnover was greater than wild type (FIG. 4D, inset).

Figure 9A:
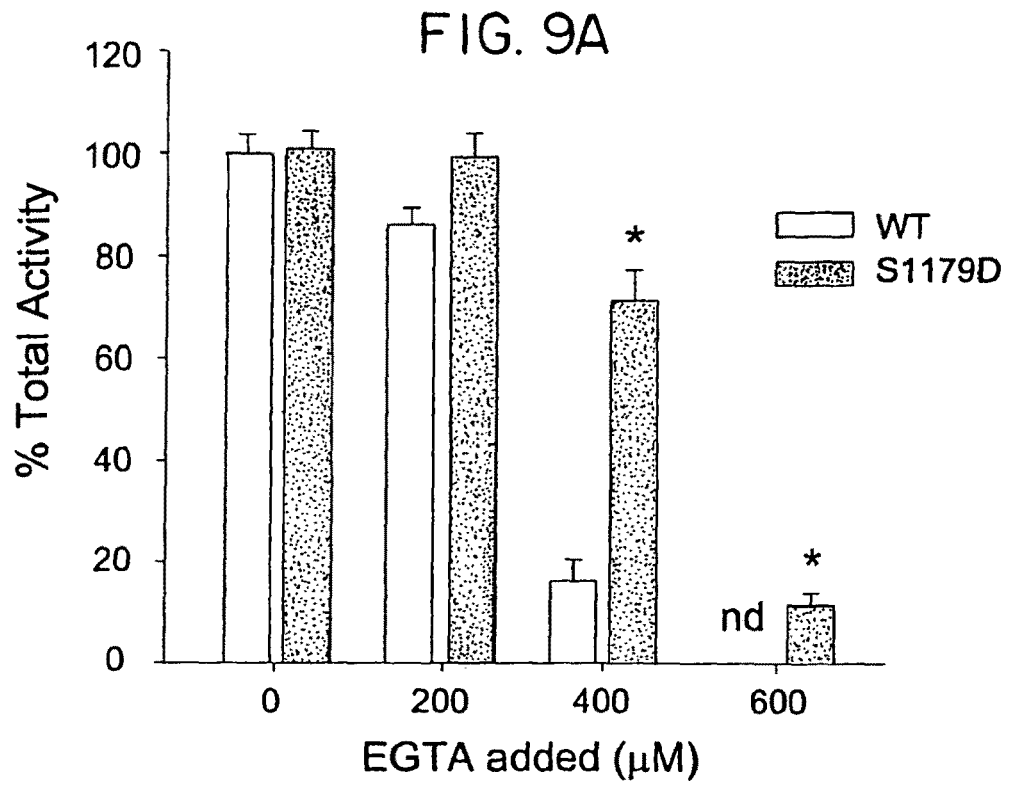
FIGS. 9A and 9B. EGTA-initiated inactivation of NOS is reduced in S1179D eNOS. Hemoglobin capture (A) and reductase assays (B) were performed as described earlier, with the following modifications. The reaction was monitored for 1 min to determine the initial rate; then, EGTA was added to the reaction mixture, and the rate was monitored for an additional 1 min. The free calcium concentration in the reaction was 200 µM, and the amount of EGTA added resulted in final concentrations of 0, 200, 400, and 600 µM chelator. The specific activities are normalized to 100% for wild type and S1179D eNOS. Values are mean±S.E., n=3-6 determinations from at least three enzyme preparations. nd, no detectable activity for wild type eNOS.
Figure 9B:
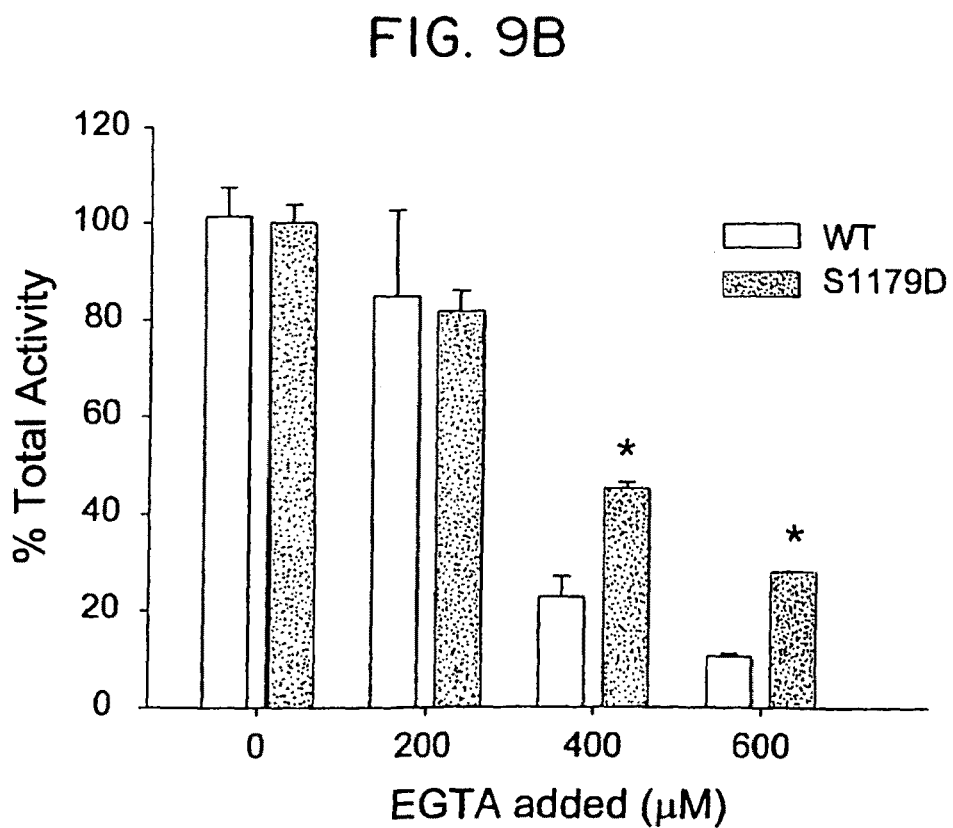

To examine whether the inactivation of S1179D eNOS was different than that of wild type enzyme, the decay in eNOS activity after chelation of calcium with EGTA was measured. In these experiments, all NOS cofactors were added in the presence of calcium (200 µM), and NO production was monitored for 1 min, followed by the addition of different concentrations of EGTA and monitoring for an additional 1 min. As seen in FIG. 9A, the addition of EGTA to wild type and S1179D eNOS reduced NO production in a concentration-dependent manner. However, NO production from S1179D eNOS was less sensitive to the addition of EGTA; i.e. wild type eNOS activity declined more rapidly at lower concentrations of EGTA than did S1179D eNOS activity. The greatest difference in activity between the enzymes was seen at 400 µM EGTA. Furthermore, at 600 µM EGTA, no activity was detected for wild type eNOS, whereas residual activity was still detected for S1179D eNOS. Similar results were obtained using cytochrome c reduction (FIG. 9B), with significant differences in activity seen with 400 and 600 µM chelator added to the reaction. However, at the highest concentration of EGTA, residual reductase activity was found for both wild type and S1179D eNOS.

In summary, bovine endothelial nitric oxide synthase (eNOS) is phosphorylated directly by the protein kinase Akt at serine 1179 (Fulton et al., 1999) and human endothelial nitric oxide synthease is phosphorylated directly by the protein kinase Akt at serine 1177 (Dimmeler et al., 1999). Mutation of residue 1179 in bovine eNOS to the negatively charged aspartate increases nitric oxide (NO) production constitutively, in the absence of agonist challenge.

It should be understood that the foregoing discussion and examples merely present a detailed description of certain preferred embodiments. It therefore should be apparent to those of ordinary skill in the art that various modifications and equivalents can be made without departing from the spirit and scope of the invention. All references, articles and patents identified above or below are herein incorporated by reference in their entirety.

REFERENCES

Additional references for which the entire citation is not given in the text are herein incorporated in their entirety.

Alessi et al., Embo J 15, 6541-6551(1996).
Bredt et al., Proc. Natl. Acad. Sci. U.S.A. 87, 682-685(1990).
Corson et al., Circulation Research 79, 984-991(1996).
Dimmeler et al., Nature 399, 601-605(1999).
Downward, Curr Opin Cell Biol 10, 262-267(1998).
Fulton et al., Nature 399, 597-601(1999).
Garcia-Cardena et al., Nature 392, 821-824(1998).
Garcia-Cardena et al., J Biol Chem 271, 27237-27240(1996).
Garcia-Cardena et al., Proc. Natl. Acad. Sci. USA 93, 6448-6453(1996a).
Huang et al, Nature 377, 239-242(1995).
Kantor et al., Science 274, 1744-1748(1996).
Kelm et al., Biochem. Biophys. Res. Commun. 154, 236-244 (1988).
Klatt et al., EMBO J. 14, 3687-3695(1995).
Liu et al., Biochemistry 35, 13277-13281(1996).
Liu et al., J. Cell Biol. 137, 1525-1535(1997).
Martasek et al., Methods Enzymol. 301, 70-78(1999).
Martasek et al., Biochem Biophys Res Commun 219, 359-365(1996).
Masters et al., Methods Enzymol. 10, 565-573(1967)
Michel et al., Proc. Natl. Acad. Sci. 90, 6252-6256(1993).
Michell et al., Curr. Biol. 9, 845-848(1999).
Murohara et al., J Clin Invest 101, 2567-2578(1998).
Papapetropoulos et al., J Clin Invest 100, 3131-3139(1997).
Roman et al., Proc. Natl. Acad. Sci. U.S.A. 92, 8428-8432 (1995).
Rudic et al., J Clin Invest 101, 731-736(1998).
Sessa et al., J Biol Chem 270, 17641-17644(1995).
Shaul et al., J Biol Chem 271, 6518-6522(1996).
Shesely et al., Proc Natl Acad Sci USA 93, 13176-13181 (1996).
Yano et al., Nature 396, 584-587(1998).

What is claimed is:

1. An isolated nucleic acid molecule encoding a variant of the endothelial nitric oxide synthase (eNOS) polypeptide of SEQ ID NO:3, wherein said variant is selected from the group consisting of a constitutively active nitric oxide synthase (NOS) polypeptide, a NOS polypeptide having an increased rate of nitric oxide (NO) production, and a NOS polypeptide having an increased reductase activity when compared with the wild-type NOS polypeptide of SEQ ID NO:3, wherein said variant consists of an amino acid mutation at the amino acid S of the consensus sequence motif RXRXXS/T.

2. The isolated nucleic acid molecule of claim 1, wherein said variant NOS polypeptide has a substituted amino acid residue at position 1177 of SEQ ID NO:3.

3. The isolated nucleic acid molecule of claim 2, wherein said variant NOS polypeptide has the amino acid sequence of SEQ ID NO:5 or wherein the amino acid residue at position 1177 of SEQ ID NO:3 is substituted with a serine residue.

4. The isolate nucleic acid molecule of claim 2, wherein (1) said variant NOS polypeptide has the amino acid sequence of SEQ ID NO:6 or wherein the serine residue of SEQ ID NO:1177 of SEQ ID NO:3 has been substituted with an aspartic acid residue or (2) said variant NOS polypeptide has the amino acid sequence of SEQ ID NO:7 or wherein the serine residue of SEQ ID NO:1177 of SEQ ID NO:3 has been substituted a glutamic acid residue.

5. The isolated nucleic acid molecule of claim 2, wherein the substituted amino acid contains an R group that comprises a phosphate group.

* * * * *

SEQUENCE LISTING

<160> NUMBER OF SEQ ID NOS: 9

<210> SEQ ID NO 1
<211> LENGTH: 8
<212> TYPE: PRT
<213> ORGANISM: Bos sp.

<400> SEQUENCE: 1

Met Gly Asn Leu Lys Ser Val Gly

-continued

```
1               5

<210> SEQ ID NO 2
<211> LENGTH: 21
<212> TYPE: PRT
<213> ORGANISM: Bos sp.

<400> SEQUENCE: 2

Arg Ile Arg Thr Gln Ser Phe Ser Leu Gln Glu Arg His Leu Arg Gly
1               5                   10                  15

Ala Val Pro Trp Ala
            20

<210> SEQ ID NO 3
<211> LENGTH: 1203
<212> TYPE: PRT
<213> ORGANISM: Homo sapiens

<400> SEQUENCE: 3

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Thr Pro Ala Pro Glu Pro Ser Arg Ala Pro Ala Ser Leu Leu Pro Pro
        35                  40                  45

Ala Pro Glu His Ser Pro Pro Ser Ser Pro Leu Thr Gln Pro Pro Glu
    50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Gln Asp Gly Pro Cys Thr Pro
                85                  90                  95

Arg Arg Cys Leu Gly Ser Leu Val Phe Pro Arg Lys Leu Gln Gly Arg
            100                 105                 110

Pro Ser Pro Gly Pro Pro Ala Pro Glu Gln Leu Leu Ser Gln Ala Arg
        115                 120                 125

Asp Phe Ile Asn Gln Tyr Tyr Ser Ser Ile Lys Arg Ser Gly Ser Gln
    130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
        195                 200                 205

Thr Tyr Ile Cys Asn His Ile Lys Tyr Ala Thr Asn Arg Gly Asn Leu
    210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
            260                 265                 270

Leu Cys Ile Gln His Gly Trp Thr Pro Gly Asn Gly Arg Phe Asp Val
        275                 280                 285

Leu Pro Leu Leu Leu Gln Ala Pro Asp Glu Pro Pro Glu Leu Phe Leu
```

```
            290                 295                 300
Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
    690                 695                 700

Ala Ala Cys Glu Thr Phe Cys Val Gly Glu Asp Ala Lys Ala Ala Ala
705                 710                 715                 720
```

-continued

```
Arg Asp Ile Phe Ser Pro Lys Arg Ser Trp Lys Arg Gln Arg Tyr Arg
            725                 730                 735
Leu Ser Ala Gln Ala Glu Gly Leu Gln Leu Leu Pro Gly Leu Ile His
            740                 745                 750
Val His Arg Arg Lys Met Phe Gln Ala Thr Ile Arg Ser Val Glu Asn
            755                 760                 765
Leu Gln Ser Ser Lys Ser Thr Arg Ala Thr Ile Leu Val Arg Leu Asp
            770                 775                 780
Thr Gly Gly Gln Glu Gly Leu Gln Tyr Gln Pro Gly Asp His Ile Gly
785                 790                 795                 800
Val Cys Pro Pro Asn Arg Pro Gly Leu Val Glu Ala Leu Leu Ser Arg
            805                 810                 815
Val Glu Asp Pro Pro Ala Pro Thr Glu Pro Val Ala Val Glu Gln Leu
            820                 825                 830
Glu Lys Gly Ser Pro Gly Gly Pro Pro Gly Trp Val Arg Asp Pro
            835                 840                 845
Arg Leu Pro Pro Cys Thr Leu Arg Gln Ala Leu Thr Phe Phe Leu Asp
    850                 855                 860
Ile Thr Ser Pro Pro Ser Pro Gln Leu Leu Arg Leu Leu Ser Thr Leu
865                 870                 875                 880
Ala Glu Glu Pro Arg Glu Gln Gln Glu Leu Glu Ala Leu Ser Gln Asp
            885                 890                 895
Pro Arg Arg Tyr Glu Glu Trp Lys Trp Phe Arg Cys Pro Thr Leu Leu
            900                 905                 910
Glu Val Leu Glu Gln Phe Pro Ser Val Ala Leu Pro Ala Pro Leu Leu
            915                 920                 925
Leu Thr Gln Leu Pro Leu Leu Gln Pro Arg Tyr Tyr Ser Val Ser Ser
            930                 935                 940
Ala Pro Ser Thr His Pro Gly Glu Ile His Leu Thr Val Ala Val Leu
945                 950                 955                 960
Ala Tyr Arg Thr Gln Asp Gly Leu Gly Pro Leu His Tyr Gly Val Cys
            965                 970                 975
Ser Thr Trp Leu Ser Gln Leu Lys Pro Gly Asp Pro Val Pro Cys Phe
            980                 985                 990
Ile Arg Gly Ala Pro Ser Phe Arg Leu Pro Pro Asp Pro Ser Leu Pro
            995                 1000                1005
Cys Ile Leu Val Gly Pro Gly Thr Gly Ile Ala Pro Phe Arg Gly
    1010                1015                1020
Phe Trp Gln Glu Arg Leu His Asp Ile Glu Ser Lys Gly Leu Gln
    1025                1030                1035
Pro Thr Pro Met Thr Leu Val Phe Gly Cys Arg Cys Ser Gln Leu
    1040                1045                1050
Asp His Leu Tyr Arg Asp Glu Val Gln Asn Ala Gln Gln Arg Gly
    1055                1060                1065
Val Phe Gly Arg Val Leu Thr Ala Phe Ser Arg Glu Pro Asp Asn
    1070                1075                1080
Pro Lys Thr Tyr Val Gln Asp Ile Leu Arg Thr Glu Leu Ala Ala
    1085                1090                1095
Glu Val His Arg Val Leu Cys Leu Glu Arg Gly His Met Phe Val
    1100                1105                1110
Cys Gly Asp Val Thr Met Ala Thr Asn Val Leu Gln Thr Val Gln
    1115                1120                1125
```

-continued

Arg Ile Leu Ala Thr Glu Gly Asp Met Glu Leu Asp Glu Ala Gly
    1130                1135                1140

Asp Val Ile Gly Val Leu Arg Asp Gln Gln Arg Tyr His Glu Asp
    1145                1150                1155

Ile Phe Gly Leu Thr Leu Arg Thr Gln Glu Val Thr Ser Arg Ile
    1160                1165                1170

Arg Thr Gln Ser Phe Ser Leu Gln Glu Arg Gln Leu Arg Gly Ala
    1175                1180                1185

Val Pro Trp Ala Phe Asp Pro Pro Gly Ser Asp Thr Asn Ser Pro
    1190                1195                1200

<210> SEQ ID NO 4
<211> LENGTH: 1205
<212> TYPE: PRT
<213> ORGANISM: Bovine

<400> SEQUENCE: 4

Met Gly Asn Leu Lys Ser Val Gly Gln Glu Pro Gly Pro Cys Gly
1               5                   10                  15

Leu Gly Leu Gly Leu Gly Leu Gly Cys Gly Lys Gln Gly Pro Ala
                20                  25                  30

Ser Pro Ala Pro Glu Pro Ser Arg Ala Pro Ala Pro Thr Pro His
                35                  40                  45

Ala Pro Asp His Ser Pro Ala Pro Asn Ser Pro Thr Leu Thr Arg Pro
        50                  55                  60

Pro Glu Gly Pro Lys Phe Pro Arg Val Lys Asn Trp Glu Leu Gly Ser
65                  70                  75                  80

Ile Thr Tyr Asp Thr Leu Cys Ala Gln Ser Gln Gln Asp Gly Pro Cys
                    85                  90                  95

Thr Pro Arg Cys Cys Leu Gly Ser Leu Val Leu Pro Arg Lys Leu Gln
                100                 105                 110

Thr Arg Pro Ser Pro Gly Pro Pro Ala Glu Gln Leu Leu Ser Gln
                115                 120                 125

Ala Arg Asp Phe Ile Asn Gln Tyr Tyr Ser Ser Ile Lys Arg Ser Gly
    130                 135                 140

Ser Gln Ala His Glu Glu Arg Leu Gln Glu Val Glu Ala Glu Val Ala
145                 150                 155                 160

Ser Thr Gly Thr Tyr His Leu Arg Glu Ser Glu Leu Val Phe Gly Ala
                    165                 170                 175

Lys Gln Ala Trp Arg Asn Ala Pro Arg Cys Val Gly Arg Ile Gln Trp
                180                 185                 190

Gly Lys Leu Gln Val Phe Asp Ala Arg Asp Cys Ser Ser Ala Gln Glu
            195                 200                 205

Met Phe Thr Tyr Ile Cys Asn His Ile Lys Tyr Ala Thr Asn Arg Gly
    210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                    245                 250                 255

Arg Gln Gln Asp Gly Ser Val Arg Gly Asp Pro Ala Asn Val Glu Ile
                260                 265                 270

Thr Glu Leu Cys Ile Gln His Gly Trp Thr Pro Gly Asn Gly Arg Phe
            275                 280                 285

Asp Val Leu Pro Leu Leu Leu Gln Ala Pro Asp Glu Ala Pro Glu Leu
    290                 295                 300

```
Phe Val Leu Pro Pro Glu Leu Val Leu Glu Val Pro Leu Glu His Pro
305                 310                 315                 320

Thr Leu Glu Trp Phe Ala Ala Leu Gly Leu Arg Trp Tyr Ala Leu Pro
                325                 330                 335

Ala Val Ser Asn Met Leu Leu Glu Ile Gly Gly Leu Glu Phe Ser Ala
            340                 345                 350

Ala Pro Phe Ser Gly Trp Tyr Met Ser Thr Glu Ile Gly Thr Arg Asn
        355                 360                 365

Leu Cys Asp Pro His Arg Tyr Asn Ile Leu Glu Asp Val Ala Val Cys
    370                 375                 380

Met Asp Leu Asp Thr Arg Thr Ser Ser Leu Trp Lys Asp Lys Ala
385                 390                 395                 400

Ala Val Glu Ile Asn Leu Ala Val Leu His Ser Phe Gln Leu Ala Lys
                405                 410                 415

Val Thr Ile Val Asp His His Ala Ala Thr Val Ser Phe Met Lys His
            420                 425                 430

Leu Asp Asn Glu Gln Lys Ala Arg Gly Gly Cys Pro Ala Asp Trp Ala
        435                 440                 445

Trp Ile Val Pro Pro Ile Ser Gly Ser Leu Thr Pro Val Phe His Gln
    450                 455                 460

Glu Met Val Asn Tyr Ile Leu Ser Pro Ala Phe Arg Tyr Gln Pro Asp
465                 470                 475                 480

Pro Trp Lys Gly Ser Ala Thr Lys Gly Ala Gly Ile Thr Arg Lys Lys
                485                 490                 495

Thr Phe Lys Glu Val Ala Asn Ala Val Lys Ile Ser Ala Ser Leu Met
            500                 505                 510

Gly Thr Leu Met Ala Lys Arg Val Lys Ala Thr Ile Leu Tyr Ala Ser
        515                 520                 525

Glu Thr Gly Arg Ala Gln Ser Tyr Ala Gln Gln Leu Gly Arg Leu Phe
        530                 535                 540

Arg Lys Ala Phe Asp Pro Arg Val Leu Cys Met Asp Glu Tyr Asp Val
545                 550                 555                 560

Val Ser Leu Glu His Glu Ala Leu Val Leu Val Val Thr Ser Thr Phe
                565                 570                 575

Gly Asn Gly Asp Pro Pro Glu Asn Gly Glu Ser Phe Ala Ala Ala Leu
            580                 585                 590

Met Glu Met Ser Gly Pro Tyr Asn Ser Ser Pro Arg Pro Glu Gln His
        595                 600                 605

Lys Ser Tyr Lys Ile Arg Phe Asn Ser Val Ser Cys Ser Asp Pro Leu
    610                 615                 620

Val Ser Ser Trp Arg Arg Lys Arg Lys Glu Ser Ser Asn Thr Asp Ser
625                 630                 635                 640

Ala Gly Ala Leu Gly Thr Leu Arg Phe Cys Gly Phe Gly Leu Gly Ser
                645                 650                 655

Arg Ala Tyr Pro His Phe Cys Ala Phe Ala Arg Ala Val Asp Thr Arg
            660                 665                 670

Leu Glu Glu Leu Gly Gly Glu Arg Leu Leu Gln Leu Gly Gln Gly Asp
        675                 680                 685

Glu Leu Cys Gly Gln Glu Glu Ala Phe Arg Gly Trp Ala Lys Ala Ala
    690                 695                 700

Phe Gln Ala Ser Cys Glu Thr Phe Cys Val Gly Glu Glu Ala Lys Ala
705                 710                 715                 720
```

-continued

```
Arg Pro Gln Asp Ile Phe Ser Pro Lys Arg Ser Trp Lys Arg Gln Arg
                725                 730                 735

Tyr Arg Leu Ser Thr Gln Ala Glu Gly Leu Gln Leu Leu Pro Gly Leu
                740                 745                 750

Ile His Val His Arg Arg Lys Met Phe Gln Ala Thr Val Leu Ser Val
                755                 760                 765

Glu Asn Leu Gln Ser Ser Lys Ser Thr Arg Ala Thr Ile Leu Val Arg
                770                 775                 780

Leu Asp Thr Ala Gly Gln Glu Gly Leu Gln Tyr Gln Pro Gly Asp His
785                 790                 795                 800

Ile Gly Ile Cys Pro Pro Asn Arg Pro Gly Leu Val Glu Ala Leu Leu
                805                 810                 815

Ser Arg Val Glu Asp Pro Pro Pro Thr Glu Ser Val Ala Val Glu
                820                 825                 830

Gln Leu Glu Lys Gly Ser Pro Gly Gly Pro Pro Ser Trp Val Arg
                835                 840                 845

Asp Pro Arg Leu Pro Pro Cys Thr Leu Arg Gln Ala Leu Thr Phe Phe
850                 855                 860

Leu Asp Ile Thr Ser Pro Pro Ser Pro Arg Leu Leu Arg Leu Leu Ser
865                 870                 875                 880

Thr Leu Ala Glu Glu Pro Ser Glu Gln Gln Glu Leu Glu Thr Leu Ser
                885                 890                 895

Gln Asp Pro Arg Arg Tyr Glu Glu Trp Lys Trp Phe Arg Cys Pro Thr
                900                 905                 910

Leu Leu Glu Val Leu Glu Gln Phe Pro Ser Val Ala Leu Pro Ala Pro
                915                 920                 925

Leu Leu Leu Thr Gln Leu Pro Leu Leu Gln Pro Arg Tyr Tyr Ser Val
                930                 935                 940

Ser Ser Ala Pro Asn Ala His Pro Gly Glu Val His Leu Thr Val Ala
945                 950                 955                 960

Val Leu Ala Tyr Arg Thr Gln Asp Gly Leu Gly Pro Leu His Tyr Gly
                965                 970                 975

Val Cys Ser Thr Trp Leu Ser Gln Leu Lys Thr Gly Asp Pro Val Pro
                980                 985                 990

Cys Phe Ile Arg Gly Ala Pro Ser Phe Arg Leu Pro Pro Asp Pro Tyr
                995                1000                1005

Val Pro Cys Ile Leu Val Gly Pro Gly Thr Gly Ile Ala Pro Phe
        1010                1015                1020

Arg Gly Phe Trp Gln Glu Arg Leu His Asp Ile Glu Ser Lys Gly
        1025                1030                1035

Leu Gln Pro Ala Pro Met Thr Leu Val Phe Gly Cys Arg Cys Ser
        1040                1045                1050

Gln Leu Asp His Leu Tyr Arg Asp Glu Val Gln Asp Ala Gln Glu
        1055                1060                1065

Arg Gly Val Phe Gly Arg Val Leu Thr Ala Phe Ser Arg Glu Pro
        1070                1075                1080

Asp Ser Pro Lys Thr Tyr Val Gln Asp Ile Leu Arg Thr Glu Leu
        1085                1090                1095

Ala Ala Glu Val His Arg Val Leu Cys Leu Glu Arg Gly His Met
        1100                1105                1110

Phe Val Cys Gly Asp Val Thr Met Ala Thr Ser Val Leu Gln Thr
        1115                1120                1125

Val Gln Arg Ile Leu Ala Thr Glu Gly Asp Met Glu Leu Asp Glu
```

-continued

```
                1130                1135                1140
Ala Gly Asp Val Ile Gly Val Leu Arg Asp Gln Gln Arg Tyr His
    1145                1150                1155
Glu Asp Ile Phe Gly Leu Thr Leu Arg Thr Gln Glu Val Thr Ser
    1160                1165                1170
Arg Ile Arg Thr Gln Ser Phe Ser Leu Gln Glu Arg His Leu Arg
    1175                1180                1185
Gly Ala Val Pro Trp Ala Phe Asp Pro Pro Gly Pro Asp Thr Pro
    1190                1195                1200
Gly Pro
    1205

<210> SEQ ID NO 5
<211> LENGTH: 1203
<212> TYPE: PRT
<213> ORGANISM: Homo sapiens
<220> FEATURE:
<221> NAME/KEY: MUTAGEN
<222> LOCATION: (1177)..(1177)
<223> OTHER INFORMATION: S is substituted

<400> SEQUENCE: 5

Met Gly Asn Leu Lys Ser Val Ala Gln Glu Pro Gly Pro Cys Gly
1               5                   10                  15
Leu Gly Leu Gly Leu Gly Leu Gly Leu Cys Gly Lys Gln Gly Pro Ala
                20                  25                  30
Thr Pro Ala Pro Glu Pro Ser Arg Ala Pro Ala Ser Leu Leu Pro Pro
            35                  40                  45
Ala Pro Glu His Ser Pro Ser Ser Pro Leu Thr Gln Pro Pro Glu
    50                  55                  60
Gly Pro Lys Phe Pro Arg Val Lys Asn Trp Glu Val Gly Ser Ile Thr
65              70                  75                  80
Tyr Asp Thr Leu Ser Ala Gln Ala Gln Gln Asp Gly Pro Cys Thr Pro
                85                  90                  95
Arg Arg Cys Leu Gly Ser Leu Val Phe Pro Arg Lys Leu Gln Gly Arg
            100                 105                 110
Pro Ser Pro Gly Pro Pro Ala Pro Glu Gln Leu Leu Ser Gln Ala Arg
        115                 120                 125
Asp Phe Ile Asn Gln Tyr Tyr Ser Ser Ile Lys Arg Ser Gly Ser Gln
    130                 135                 140
Ala His Glu Gln Arg Leu Gln Glu Val Glu Ala Glu Val Ala Ala Thr
145                 150                 155                 160
Gly Thr Tyr Gln Leu Arg Glu Ser Glu Leu Val Phe Gly Ala Lys Gln
                165                 170                 175
Ala Trp Arg Asn Ala Pro Arg Cys Val Gly Arg Ile Gln Trp Gly Lys
            180                 185                 190
Leu Gln Val Phe Asp Ala Arg Asp Cys Arg Ser Ala Gln Glu Met Phe
        195                 200                 205
Thr Tyr Ile Cys Asn His Ile Lys Tyr Ala Thr Asn Arg Gly Asn Leu
    210                 215                 220
Arg Ser Ala Ile Thr Val Phe Pro Gln Arg Cys Pro Gly Arg Gly Asp
225                 230                 235                 240
Phe Arg Ile Trp Asn Ser Gln Leu Val Arg Tyr Ala Gly Tyr Arg Gln
                245                 250                 255
Gln Asp Gly Ser Val Arg Gly Asp Pro Ala Asn Val Glu Ile Thr Glu
            260                 265                 270
```

Leu Cys Ile Gln His Gly Trp Thr Pro Gly Asn Gly Arg Phe Asp Val
            275                 280                 285

Leu Pro Leu Leu Leu Gln Ala Pro Asp Glu Pro Pro Glu Leu Phe Leu
            290                 295                 300

Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
            355                 360                 365

Asp Pro His Arg Tyr Asn Ile Leu Glu Asp Val Ala Val Cys Met Asp
            370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
            435                 440                 445

Val Pro Pro Ile Ser Gly Ser Leu Thr Pro Val Phe His Gln Glu Met
450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
            515                 520                 525

Gly Arg Ala Gln Ser Tyr Ala Gln Gln Leu Gly Arg Leu Phe Arg Lys
            530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
            595                 600                 605

Tyr Lys Ile Arg Phe Asn Ser Ile Ser Cys Ser Asp Pro Leu Val Ser
            610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
            675                 680                 685

```
Cys Gly Gln Glu Glu Ala Phe Arg Gly Trp Ala Gln Ala Ala Phe Gln
690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
            725                 730                 735

Leu Ser Ala Gln Ala Glu Gly Leu Gln Leu Leu Pro Gly Leu Ile His
                740                 745                 750

Val His Arg Arg Lys Met Phe Gln Ala Thr Ile Arg Ser Val Glu Asn
            755                 760                 765

Leu Gln Ser Ser Lys Ser Thr Arg Ala Thr Ile Leu Val Arg Leu Asp
770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
            820                 825                 830

Glu Lys Gly Ser Pro Gly Gly Pro Pro Gly Trp Val Arg Asp Pro
            835                 840                 845

Arg Leu Pro Pro Cys Thr Leu Arg Gln Ala Leu Thr Phe Phe Leu Asp
850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Leu Glu Ala Leu Ser Gln Asp
                885                 890                 895

Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
            915                 920                 925

Leu Thr Gln Leu Pro Leu Leu Gln Pro Arg Tyr Tyr Ser Val Ser Ser
    930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
                965                 970                 975

Ser Thr Trp Leu Ser Gln Leu Lys Pro Gly Asp Pro Val Pro Cys Phe
            980                 985                 990

Ile Arg Gly Ala Pro Ser Phe Arg Leu Pro Pro Asp Pro Ser Leu Pro
            995                 1000                1005

Cys Ile Leu Val Gly Pro Gly Thr Gly Ile Ala Pro Phe Arg Gly
    1010                1015                1020

Phe Trp Gln Glu Arg Leu His Asp Ile Glu Ser Lys Gly Leu Gln
    1025                1030                1035

Pro Thr Pro Met Thr Leu Val Phe Gly Cys Arg Cys Ser Gln Leu
    1040                1045                1050

Asp His Leu Tyr Arg Asp Glu Val Gln Asn Ala Gln Gln Arg Gly
    1055                1060                1065

Val Phe Gly Arg Val Leu Thr Ala Phe Ser Arg Glu Pro Asp Asn
    1070                1075                1080

Pro Lys Thr Tyr Val Gln Asp Ile Leu Arg Thr Glu Leu Ala Ala
    1085                1090                1095

Glu Val His Arg Val Leu Cys Leu Glu Arg Gly His Met Phe Val
```

-continued

```
                1100                1105                1110
Cys Gly Asp Val Thr Met Ala Thr Asn Val Leu Gln Thr Val Gln
    1115                1120                1125

Arg Ile Leu Ala Thr Glu Gly Asp Met Glu Leu Asp Glu Ala Gly
    1130                1135                1140

Asp Val Ile Gly Val Leu Arg Asp Gln Gln Arg Tyr His Glu Asp
    1145                1150                1155

Ile Phe Gly Leu Thr Leu Arg Thr Gln Glu Val Thr Ser Arg Ile
    1160                1165                1170

Arg Thr Gln Ser Phe Ser Leu Gln Glu Arg Gln Leu Arg Gly Ala
    1175                1180                1185

Val Pro Trp Ala Phe Asp Pro Pro Gly Ser Asp Thr Asn Ser Pro
    1190                1195                1200

<210> SEQ ID NO 6
<211> LENGTH: 1203
<212> TYPE: PRT
<213> ORGANISM: Homo sapiens

<400> SEQUENCE: 6

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Thr Pro Ala Pro Glu Pro Ser Arg Ala Pro Ala Ser Leu Leu Pro Pro
        35                  40                  45

Ala Pro Glu His Ser Pro Pro Ser Ser Pro Leu Thr Gln Pro Pro Glu
    50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Gln Asp Gly Pro Cys Thr Pro
                85                  90                  95

Arg Arg Cys Leu Gly Ser Leu Val Phe Pro Arg Lys Leu Gln Gly Arg
            100                 105                 110

Pro Ser Pro Gly Pro Pro Ala Pro Glu Gln Leu Leu Ser Gln Ala Arg
        115                 120                 125

Asp Phe Ile Asn Gln Tyr Tyr Ser Ser Ile Lys Arg Ser Gly Ser Gln
    130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
        195                 200                 205

Thr Tyr Ile Cys Asn His Ile Lys Tyr Ala Thr Asn Arg Gly Asn Leu
    210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
            260                 265                 270
```

```
Leu Cys Ile Gln His Gly Trp Thr Pro Gly Asn Gly Arg Phe Asp Val
        275                 280                 285

Leu Pro Leu Leu Leu Gln Ala Pro Asp Glu Pro Pro Glu Leu Phe Leu
290                 295                 300

Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
```

-continued

```
            690             695             700
Ala Ala Cys Glu Thr Phe Cys Val Gly Glu Asp Ala Lys Ala Ala
705             710             715             720

Arg Asp Ile Phe Ser Pro Lys Arg Ser Trp Lys Arg Gln Arg Tyr Arg
            725             730             735

Leu Ser Ala Gln Ala Glu Gly Leu Gln Leu Leu Pro Gly Leu Ile His
            740             745             750

Val His Arg Arg Lys Met Phe Gln Ala Thr Ile Arg Ser Val Glu Asn
            755             760             765

Leu Gln Ser Ser Lys Ser Thr Arg Ala Thr Ile Leu Val Arg Leu Asp
770             775             780

Thr Gly Gln Glu Gly Leu Gln Tyr Gln Pro Gly Asp His Ile Gly
785             790             795             800

Val Cys Pro Pro Asn Arg Pro Gly Leu Val Glu Ala Leu Leu Ser Arg
            805             810             815

Val Glu Asp Pro Ala Pro Thr Glu Pro Val Ala Val Glu Gln Leu
            820             825             830

Glu Lys Gly Ser Pro Gly Gly Pro Pro Gly Trp Val Arg Asp Pro
            835             840             845

Arg Leu Pro Pro Cys Thr Leu Arg Gln Ala Leu Thr Phe Phe Leu Asp
850             855             860

Ile Thr Ser Pro Pro Ser Pro Gln Leu Leu Arg Leu Leu Ser Thr Leu
865             870             875             880

Ala Glu Glu Pro Arg Glu Gln Gln Glu Leu Glu Ala Leu Ser Gln Asp
            885             890             895

Pro Arg Arg Tyr Glu Glu Trp Lys Trp Phe Arg Cys Pro Thr Leu Leu
            900             905             910

Glu Val Leu Glu Gln Phe Pro Ser Val Ala Leu Pro Ala Pro Leu Leu
            915             920             925

Leu Thr Gln Leu Pro Leu Leu Gln Pro Arg Tyr Tyr Ser Val Ser Ser
            930             935             940

Ala Pro Ser Thr His Pro Gly Glu Ile His Leu Thr Val Ala Val Leu
945             950             955             960

Ala Tyr Arg Thr Gln Asp Gly Leu Gly Pro Leu His Tyr Gly Val Cys
            965             970             975

Ser Thr Trp Leu Ser Gln Leu Lys Pro Gly Asp Pro Val Pro Cys Phe
            980             985             990

Ile Arg Gly Ala Pro Ser Phe Arg Leu Pro Pro Asp Pro Ser Leu Pro
            995             1000            1005

Cys Ile Leu Val Gly Pro Gly Thr Gly Ile Ala Pro Phe Arg Gly
            1010            1015            1020

Phe Trp Gln Glu Arg Leu His Asp Ile Glu Ser Lys Gly Leu Gln
            1025            1030            1035

Pro Thr Pro Met Thr Leu Val Phe Gly Cys Arg Cys Ser Gln Leu
            1040            1045            1050

Asp His Leu Tyr Arg Asp Glu Val Gln Asn Ala Gln Gln Arg Gly
            1055            1060            1065

Val Phe Gly Arg Val Leu Thr Ala Phe Ser Arg Glu Pro Asp Asn
            1070            1075            1080

Pro Lys Thr Tyr Val Gln Asp Ile Leu Arg Thr Glu Leu Ala Ala
            1085            1090            1095

Glu Val His Arg Val Leu Cys Leu Glu Arg Gly His Met Phe Val
            1100            1105            1110
```

```
Cys Gly Asp Val Thr Met Ala Thr Asn Val Leu Gln Thr Val Gln
    1115                1120                1125

Arg Ile Leu Ala Thr Glu Gly Asp Met Glu Leu Asp Glu Ala Gly
    1130                1135                1140

Asp Val Ile Gly Val Leu Arg Asp Gln Gln Arg Tyr His Glu Asp
    1145                1150                1155

Ile Phe Gly Leu Thr Leu Arg Thr Gln Glu Val Thr Ser Arg Ile
    1160                1165                1170

Arg Thr Gln Asp Phe Ser Leu Gln Glu Arg Gln Leu Arg Gly Ala
    1175                1180                1185

Val Pro Trp Ala Phe Asp Pro Pro Gly Ser Asp Thr Asn Ser Pro
    1190                1195                1200

<210> SEQ ID NO 7
<211> LENGTH: 1203
<212> TYPE: PRT
<213> ORGANISM: Homo sapiens

<400> SEQUENCE: 7

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
                20                  25                  30

Thr Pro Ala Pro Glu Pro Ser Arg Ala Pro Ala Ser Leu Leu Pro Pro
            35                  40                  45

Ala Pro Glu His Ser Pro Pro Ser Ser Pro Leu Thr Gln Pro Pro Glu
        50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Asp Gly Pro Cys Thr Pro
                    85                  90                  95

Arg Arg Cys Leu Gly Ser Leu Val Phe Pro Arg Lys Leu Gln Gly Arg
                100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
        130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
                180                 185                 190

Leu Gln Val Phe Asp Ala Arg Asp Cys Arg Ser Ala Gln Glu Met Phe
            195                 200                 205

Thr Tyr Ile Cys Asn His Ile Lys Tyr Ala Thr Asn Arg Gly Asn Leu
        210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
                260                 265                 270

Leu Cys Ile Gln His Gly Trp Thr Pro Gly Asn Gly Arg Phe Asp Val
```

-continued

```
                275                 280                 285
Leu Pro Leu Leu Gln Ala Pro Asp Glu Pro Glu Leu Phe Leu
    290                 295                 300
Leu Pro Pro Glu Leu Val Leu Glu Val Pro Leu Glu His Pro Thr Leu
305                 310                 315                 320
Glu Trp Phe Ala Ala Leu Gly Leu Arg Trp Tyr Ala Leu Pro Ala Val
                325                 330                 335
Ser Asn Met Leu Leu Glu Ile Gly Gly Leu Glu Phe Pro Ala Ala Pro
                340                 345                 350
Phe Ser Gly Trp Tyr Met Ser Thr Glu Ile Gly Thr Arg Asn Leu Cys
                355                 360                 365
Asp Pro His Arg Tyr Asn Ile Leu Glu Asp Val Ala Val Cys Met Asp
            370                 375                 380
Leu Asp Thr Arg Thr Thr Ser Ser Leu Trp Lys Asp Lys Ala Ala Val
385                 390                 395                 400
Glu Ile Asn Val Ala Val Leu His Ser Tyr Gln Leu Ala Lys Val Thr
                    405                 410                 415
Ile Val Asp His His Ala Ala Thr Ala Ser Phe Met Lys His Leu Glu
                420                 425                 430
Asn Glu Gln Lys Ala Arg Gly Gly Cys Pro Ala Asp Trp Ala Trp Ile
            435                 440                 445
Val Pro Pro Ile Ser Gly Ser Leu Thr Pro Val Phe His Gln Glu Met
    450                 455                 460
Val Asn Tyr Phe Leu Ser Pro Ala Phe Arg Tyr Gln Pro Asp Pro Trp
465                 470                 475                 480
Lys Gly Ser Ala Ala Lys Gly Thr Gly Ile Thr Arg Lys Lys Thr Phe
                485                 490                 495
Lys Glu Val Ala Asn Ala Val Lys Ile Ser Ala Ser Leu Met Gly Thr
                500                 505                 510
Val Met Ala Lys Arg Val Lys Ala Thr Ile Leu Tyr Gly Ser Glu Thr
            515                 520                 525
Gly Arg Ala Gln Ser Tyr Ala Gln Gln Leu Gly Arg Leu Phe Arg Lys
    530                 535                 540
Ala Phe Asp Pro Arg Val Leu Cys Met Asp Glu Tyr Asp Val Val Ser
545                 550                 555                 560
Leu Glu His Glu Thr Leu Val Leu Val Val Thr Ser Thr Phe Gly Asn
                565                 570                 575
Gly Asp Pro Pro Glu Asn Gly Glu Ser Phe Ala Ala Ala Leu Met Glu
                580                 585                 590
Met Ser Gly Pro Tyr Asn Ser Ser Pro Arg Pro Glu Gln His Lys Ser
                595                 600                 605
Tyr Lys Ile Arg Phe Asn Ser Ile Ser Cys Ser Asp Pro Leu Val Ser
            610                 615                 620
Ser Trp Arg Arg Lys Arg Lys Glu Ser Ser Asn Thr Asp Ser Ala Gly
625                 630                 635                 640
Ala Leu Gly Thr Leu Arg Phe Cys Val Phe Gly Leu Gly Ser Arg Ala
                645                 650                 655
Tyr Pro His Phe Cys Ala Phe Ala Arg Ala Val Asp Thr Arg Leu Glu
                660                 665                 670
Glu Leu Gly Gly Glu Arg Leu Leu Gln Leu Gly Gln Gly Asp Glu Leu
            675                 680                 685
Cys Gly Gln Glu Glu Ala Phe Arg Gly Trp Ala Gln Ala Ala Phe Gln
    690                 695                 700
```

```
Ala Ala Cys Glu Thr Phe Cys Val Gly Glu Asp Ala Lys Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His
            740                 745                 750

Val His Arg Arg Lys Met Phe Gln Ala Thr Ile Arg Ser Val Glu Asn
                755                 760                 765

Leu Gln Ser Ser Lys Ser Thr Arg Ala Thr Ile Leu Val Arg Leu Asp
            770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
            820                 825                 830

Glu Lys Gly Ser Pro Gly Gly Pro Pro Pro Gly Trp Val Arg Asp Pro
835                 840                 845

Arg Leu Pro Pro Cys Thr Leu Arg Gln Ala Leu Thr Phe Phe Leu Asp
            850                 855                 860

Ile Thr Ser Pro Ser Pro Gln Leu Leu Arg Leu Leu Ser Thr Leu
865                 870                 875                 880

Ala Glu Glu Pro Arg Glu Gln Gln Glu Leu Glu Ala Leu Ser Gln Asp
                885                 890                 895

Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
                915                 920                 925

Leu Thr Gln Leu Pro Leu Leu Gln Pro Arg Tyr Tyr Ser Val Ser Ser
            930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
                965                 970                 975

Ser Thr Trp Leu Ser Gln Leu Lys Pro Gly Asp Pro Val Pro Cys Phe
            980                 985                 990

Ile Arg Gly Ala Pro Ser Phe Arg Leu Pro Pro Asp Pro Ser Leu Pro
                995                 1000                1005

Cys Ile Leu Val Gly Pro Gly Thr Gly Ile Ala Pro Phe Arg Gly
    1010                1015                1020

Phe Trp Gln Glu Arg Leu His Asp Ile Glu Ser Lys Gly Leu Gln
    1025                1030                1035

Pro Thr Pro Met Thr Leu Val Phe Gly Cys Arg Cys Ser Gln Leu
    1040                1045                1050

Asp His Leu Tyr Arg Asp Glu Val Gln Asn Ala Gln Gln Arg Gly
    1055                1060                1065

Val Phe Gly Arg Val Leu Thr Ala Phe Ser Arg Glu Pro Asp Asn
    1070                1075                1080

Pro Lys Thr Tyr Val Gln Asp Ile Leu Arg Thr Glu Leu Ala Ala
    1085                1090                1095

Glu Val His Arg Val Leu Cys Leu Glu Arg Gly His Met Phe Val
    1100                1105                1110
```

| Cys | Gly | Asp | Val | Thr | Met | Ala | Thr | Asn | Val | Leu | Gln | Thr | Val | Gln |
| 1115 | | | | | 1120 | | | | | 1125 | | | | |

| Arg | Ile | Leu | Ala | Thr | Glu | Gly | Asp | Met | Glu | Leu | Asp | Glu | Ala | Gly |
| 1130 | | | | | 1135 | | | | | 1140 | | | | |

| Asp | Val | Ile | Gly | Val | Leu | Arg | Asp | Gln | Gln | Arg | Tyr | His | Glu | Asp |
| 1145 | | | | | 1150 | | | | | 1155 | | | | |

| Ile | Phe | Gly | Leu | Thr | Leu | Arg | Thr | Gln | Glu | Val | Thr | Ser | Arg | Ile |
| 1160 | | | | | 1165 | | | | | 1170 | | | | |

| Arg | Thr | Gln | Glu | Phe | Ser | Leu | Gln | Glu | Arg | Gln | Leu | Arg | Gly | Ala |
| 1175 | | | | | 1180 | | | | | 1185 | | | | |

| Val | Pro | Trp | Ala | Phe | Asp | Pro | Pro | Gly | Ser | Asp | Thr | Asn | Ser | Pro |
| 1190 | | | | | 1195 | | | | | 1200 | | | | |

<210> SEQ ID NO 8
<211> LENGTH: 3612
<212> TYPE: DNA
<213> ORGANISM: Homo sapiens

<400> SEQUENCE: 8

```
atgggcaact tgaagagcgt ggcccaggag cctgggccac cctgcggcct ggggctgggg      60
ctgggccttg gctgtgcgg caagcagggc ccagccaccc cggcccctga gcccagccgg     120
gccccagcat ccctactccc accagcgcca gaacacagcc cccgagctc cccgctaacc     180
cagcccccag aggggcccaa gttccctcgt gtgaagaact gggaggtggg gagcatcacc     240
tatgacaccc tcagcgccca ggcgcagcag gatgggccct gcaccccaag acgctgcctg     300
ggctccctgg tatttccacg gaaactacag gccggccct ccccggccc ccggccct        360
gagcagctgc tgagtcaggc ccgggactc atcaaccagt actacagctc cattaagagg     420
agcggctccc aggcccacga cagcggctt caagaggtgg aagccgaggt ggcagccaca     480
ggcacctacc agcttaggga gagcgagctg gtgttcgggg ctaagcaggc ctggcgcaac     540
gctccccgct gcgtgggccg gatccagtgg gggaagctgc aggtgttcga tgcccgggac     600
tgcaggtctg cacaggaaat gttcacctac atctgcaacc acatcaagta tgccaccaac     660
cggggcaacc ttcgctcggc catcacagtg ttcccgcagc gctgccctgg ccgaggagac     720
ttccgaatct ggaacagcca gctggtgcgc tacgcgggct accggcagca ggacggctct     780
gtgcggggg acccagccaa cgtggagatc accgagctct gcattcagca cggctggacc     840
ccaggaaacg tcgcttcga cgtgctgccc ctgctgctgc aggccccaga tgagccccca     900
gaactcttcc ttctgccccc cgagctggtc cttgaggtgc ccctggagca ccccacgctg     960
gagtggtttg cagccctggg cctgcgctgg tacgccctcc cggcagtgtc caacatgctg    1020
ctggaaattg gggcctgga gttccccgca gcccccttca gtggctggta catgagcact    1080
gagatcggca cgaggaacct gtgtgaccct caccgctaca acatcctgga ggatgtggct    1140
gtctgcatgg acctggatac ccggaccacc tcgtccctgt ggaaagacaa ggcagcagtg    1200
gaaatcaacg tggccgtgct gcacagttac cagctagcca agtcaccat cgtggaccac    1260
cacgccgcca cggcctcttt catgaagcac ctggagaatg agcagaaggc cagggggggc    1320
tgccctgcag actgggcctg gatcgtgccc ccatctcgg gcagcctcac tcctgttttc    1380
catcaggaga tggtcaacta tttcctgtcc ccggccttcc gctaccagcc agaccccgg    1440
aaggggagtg ccgccaaggg caccggcatc accaggaaga gacctttaa agaagtggcc    1500
aacgccgtga gatctccgc ctcgctcatg ggcacggtga tggcgaagcg agtgaaggcg    1560
acaatcctgt atgctccga gaccggccgg gcccagagct acgcacagca gctggggaga    1620
```

```
ctcttccgga aggcttttga tccccgggtc ctgtgtatgg atgagtatga cgtggtgtcc      1680
ctcgaacacg agacgctggt gctggtggta accagcacat ttgggaatgg ggatccccg       1740 gagaatggag agagctttgc agctgccctg atggagatgt ccggcccta caacagctcc      1800 cctcggccgg aacagcacaa gagttataag atccgcttca acagcatctc ctgctcagac     1860
ccactggtgt cctcttggcg gcggaagagg aaggagtcca gtaacacaga cagtgcaggg     1920
gccctgggca ccctcaggtt ctgtgtgttc gggctcggct cccgggcata ccccacttc      1980 tgcgcctttg ctcgtgccgt ggacacacg ctggaggaac tgggcgggga gcggctgctg       2040
cagctgggcc agggcgacga gctgtgcggc caggaggagg ccttccgagg ctgggcccag     2100
gctgccttcc aggccgcctg tgagaccttc tgtgtgggag aggatgccaa ggccgccgcc     2160
cgagacatct tcagccccaa acggagctgg aagcgccaga ggtaccggct gagcgcccag     2220
gccgagggcc tgcagttgct gccaggtctg atccacgtgc acaggcggaa gatgttccag     2280
gctacaatcc gctcagtgga aaacctgcaa agcagcaagt ccacgagggc caccatcctg     2340
gtgcgcctgg acaccggagg ccaggagggg ctgcagtacc agccggggga ccacataggt     2400
gtctgcccgc ccaaccggcc cggccttgtg gaggcgctgc tgagccgcgt ggaggacccg     2460
ccggcgccca ctgagcccgt ggcagtagag cagctggaga agggcagccc tggtggccct     2520
ccccccggct gggtgcggga cccccggctg ccccgtgca cgctgcgcca ggctctcacc       2580
ttcttcctgg acatcacctc cccacccagc cctcagctct gcggctgct cagcaccttg      2640 gcagaagagc ccagggaaca gcaggagctg gaggccctca gccaggatcc ccgacgctac     2700
gaggagtgga gtggttccg ctgccccacg ctgctggagg tgctggagca gttcccgtcg      2760
gtggcgctgc ctgccccact gctcctcacc cagctgcctc tgctcagcc ccggtactac      2820 tcagtcagct cggcacccag cacccaccca ggagagatcc acctcactgt agctgtgctg     2880
gcatacagga ctcaggatgg gctgggcccc ctgcactatg gagtctgctc cacgtggcta     2940
agccagctca agcccggaga ccctgtgccc tgcttcatcc ggggggctcc ctccttccgg     3000
ctgccacccg atcccagctt gccctgcatc ctggtgggtc caggcactgg cattgccccc     3060
ttccggggat tctggcagga gcggctgcat gacattgaga gcaaagggct gcagcccact     3120
cccatgactt tggtgttcgg ctgccgatgc tcccaacttg accatctcta ccgcgacgag     3180
gtgcagaacg cccagcagcg cggggtgttt ggccgagtcc tcaccgcctt ctcccgggaa     3240
cctgacaacc ccaagaccta cgtgcaggac atcctgagga cggagctggc tgcggaggtg     3300
caccgcgtgc tgtgcctcga gcggggccac atgtttgtct gcggcgatgt taccatggca     3360
accaacgtcc tgcagaccgt gcagcgcatc ctggcgacgg agggcgacat ggagctggac     3420
gaggccggcg acgtcatcgg cgtgctgcgg gatcagcaac gctaccacga agacattttc     3480
gggctcacgc tgcgcaccca ggaggtgaca agccgcatac gcacccagag cttttccttg     3540
caggagcgtc agttgcgggg cgcagtgccc tgggcgttcg accctcccgg ctcagacacc     3600
aacagcccct ga                                                          3612

<210> SEQ ID NO 9
<211> LENGTH: 4077
<212> TYPE: DNA
<213> ORGANISM: Homo sapiens

<400> SEQUENCE: 9
gaattcccac tctgctgcct gctccagcag acggacgcac agtaacatgg gcaacttgaa       60
```

-continued

```
gagcgtggcc caggagcctg ggccaccctg cggcctgggg ctggggctgg gccttgggct      120
gtgcggcaag cagggcccag ccaccccggc ccctgagccc agccgggccc cagcatccct      180
actcccacca gcgccagaac acagcccccc gagctccccg ctaacccagc ccccagaggg      240
gcccaagttc cctcgtgtga agaactggga ggtggggagc atcacctatg acaccctcag      300
cgcccaggcg cagcaggatg ggccctgcac ccaagacgc tgcctgggct ccctggtatt       360
tccacggaaa ctacagggcc ggcctccccc ggcccccccg ccccctgagc agctgctgag      420
tcaggcccgg gacttcatca accagtacta cagctccatt aagaggagcg ctcccaggc      480
ccacgaacag cggcttcaag aggtggaagc cgaggtggca gccacaggca cctaccagct     540
tagggagagc gagctggtgt tcggggctaa gcaggcctgg cgcaacgctc cccgctgcgt     600
gggccggatc cagtggggga agctgcaggt gttcgatgcc cgggactgca ggtctgcaca    660
ggaaatgttc acctacatct gcaaccacat caagtatgcc accaaccggg caaccttcg     720
ctcggccatc acagtgttcc cgcagcgctg ccctggccga ggagacttcc gaatctggaa    780
cagccagctg gtgcgctacg cgggctaccg gcagcaggac ggctctgtgc gggggggacccc  840
agccaacgtg gagatcaccg agctctgcat tcagcacggc tggaccccag gaaacggtcg    900
cttcgacgtg ctgccctgc tgctgcaggc cccagatgag ccccagaac tcttccttct     960
gcccccgag ctggtccttg aggtgcccct ggagcacccc acgctggagt ggtttgcagc    1020
cctgggcctg cgctggtacg ccctcccggc agtgtccaac atgctgctgg aaattggggg   1080
cctggagttc cccgcagccc ccttcagtgg ctggtacatg agcactgaga tcggcacgag  1140
gaacctgtgt gaccctcacc gctacaacat cctggaggat gtggctgtct gcatggacct   1200
ggatacccgg accacctcgt ccctgtggaa agacaaggca gcagtggaaa tcaacgtggc   1260
cgtgctgcac agttaccagc tagccaaagt caccatcgtg gaccaccacg ccgccacggc   1320
ctctttcatg aagcacctgg agaatgagca gaaggccagg gggggctgcc ctgcagactg   1380
ggcctggatc gtgccccca tctcgggcag cctcactcct gttttccatc aggagatggt    1440
caactatttc ctgtccccgg ccttccgcta ccagccagac ccctggaagg ggagtgccgc   1500
caagggcacc ggcatcacca ggaagaagac ctttaaagaa gtggccaacg ccgtgaagat   1560
ctccgcctcg ctcatgggca cggtgatggc gaagcgagtg aaggcgacaa tcctgtatgg    1620
ctccgagacc ggccgggccc agagctacgc acagcagctg gggagactct tccggaaggc    1680
ttttgatccc cgggtcctgt gtatggatga gtatgacgtg gtgtccctcg aaacgagac    1740
gctggtgctg gtggtaacca gcacatttgg gaatggggat cccccggaga atggagagag   1800
ctttgcagct gccctgatgg agatgtccgg cccctacaac agctccctc ggccggaaca    1860
gcacaagagt tataagatcc gcttcaacag catctcctgc tcagacccac tggtgtcctc    1920
ttggcggcgg aagaggaagg agtccagtaa cacagacagt gcaggggccc tgggcaccct   1980
caggttctgt gtgttcggc tcggctcccg ggcataccc cacttctgcg cctttgctcg    2040
tgccgtggac acacggctgg aggaactggg cggggagcgg ctgctgcagc tgggccaggg   2100
cgacgagctg tgcggccagg aggaggcctt ccgaggctgg gccaggctg ccttccagcc    2160
cgcctgtgag accttctgtg tgggagagga tgccaaggcc gccgcccgag acatcttcag   2220
ccccaaacgg agctggaagc gccagaggta ccggctgagc gcccaggccg agggcctgca   2280
gttgctgcca ggtctgatcc acgtgcacag gcggaagatg ttccaggcta caatccgctc   2340
agtggaaaac ctgcaaagca gcaagtccac gagggccacc atcctggtgc gcctggacac   2400
cggaggccag gaggggctgc agtaccagcc gggggaccac ataggtgtct gccgcgccaa   2460
```

```
ccggcccggc cttgtggagg cgctgctgag ccgcgtggag gacccgccgg cgcccactga    2520
gcccgtggca gtagagcagc tggagaaggg cagccctggt ggcctcccc ccggctgggt     2580 gcgggacccc cggctgcccc cgtgcacgct gcgccaggct ctcaccttct tcctggacat    2640
cacctcccca cccagccctc agctcttgcg gctgctcagc accttggcag aagagcccag    2700
ggaacagcag gagctggagg ccctcagcca ggatccccga cgctacgagg agtggaagtg    2760
gttccgctgc cccacgctgc tggaggtgct ggagcagttc ccgtcggtgg cgctgcctgc    2820
cccactgctc ctcacccagc tgcctctgct ccagccccgg tactactcag tcagctcggc    2880
acccagcacc cacccaggag agatccacct cactgtagct gtgctggcat acaggactca    2940
ggatgggctg ggcccctgc actatggagt ctgctccacg tggctaagcc agctcaagcc     3000
cggagaccct gtgccctgct tcatccgggg ggctccctcc ttccggctgc cacccgatcc    3060
cagcttgccc tgcatcctgg tgggtccagg cactggcatt gccccttcc ggggattctg     3120 gcaggagcgg ctgcatgaca ttgagagcaa agggctgcag cccactccca tgactttggt    3180
gttcggctgc cgatgctccc aacttgacca tctctaccgc gacgaggtgc agaacgccca    3240
gcagcgcggg gtgtttggcc gagtcctcac cgccttctcc cgggaacctg acaacccca     3300 gacctacgtg caggacatcc tgaggacgga gctggctgcg gaggtgcacc gcgtgctgtg    3360
cctcgagcgg ggccacatgt ttgtctgcgg cgatgttacc atggcaacca acgtcctgca    3420
gaccgtgcag cgcatcctgg cgacggaggg cgacatggag ctggacgagg ccggcgacgt    3480
catcggcgtg ctgcgggatc agcaacgcta ccacgaagac attttcgggc tcacgctgcg    3540
cacccaggag gtgacaagcc gcatacgcac ccagagcttt tccttgcagg agcgtcagtt    3600
gcggggcgca gtgccctggg cgttcgaccc tcccggctca gacaccaaca gcccctgaga    3660
gccgcctggc tttcccttcc agttccggga gagcggctgc ccgactcagg tccgcccgac    3720
caggatcagc cccgctcctc ccctcttgag gtggtgcctt ctcacatctg tccagaggct    3780
gcaaggattc agcattattc ctccaggaag gagcaaaacg cctctttcc ctctctaggc     3840 ctgttgcctc gggcctgggt ccgccttaat ctggaaggcc cctcccagca gcggtacccc    3900
agggcctact gccacccgct tcctgtttct tagtccgaat gttagattcc tcttgcctct    3960
ctcaggagta tcttacctgt aaagtctaat ctctaaatca agtatttatt attgaagatt    4020
taccataagg gactgtgcca gatgttagga gaactactaa agtgcctacc ccagctc      4077
```